(12) United States Patent
Mass et al.

(10) Patent No.: US 8,437,854 B2
(45) Date of Patent: May 7, 2013

(54) REGULATORY COMPLIANT TRANSMISSION OF MEDICAL DATA EMPLOYING A PATIENT IMPLANTABLE MEDICAL DEVICE AND A GENERIC NETWORK ACCESS DEVICE

(75) Inventors: William Mass, Renton, WA (US); Greg P. Carpenter, Centerville, MN (US); Daniel Kollmann, Andover, MN (US); Arthur Lai, Minnetonka, MN (US); Philip G. Dion, Blaine, MN (US); Thomas Phillips, Stanchfield, MN (US); Aaron Eash, Dallas, TX (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/610,324

(22) Filed: Sep. 11, 2012

(65) Prior Publication Data

US 2013/0007210 A1    Jan. 3, 2013

Related U.S. Application Data

(63) Continuation of application No. 13/357,399, filed on Jan. 24, 2012, now Pat. No. 8,265,757, which is a continuation of application No. 12/435,866, filed on May 5, 2009, now Pat. No. 8,103,346.

(60) Provisional application No. 61/128,583, filed on May 22, 2008.

(51) Int. Cl.
*A61N 1/00* (2006.01)

(52) U.S. Cl.
USPC ......................................................... 607/32

(58) Field of Classification Search .................. 607/32, 607/30; 600/300; 705/2; 709/205
See application file for complete search history.

(56) References Cited

U.S. PATENT DOCUMENTS

| | | | |
|---|---|---|---|
| 5,720,770 | A | 2/1998 | Nappholz |
| 5,729,203 | A | 3/1998 | Oka |
| 5,752,976 | A | 5/1998 | Duffin et al. |
| 6,083,248 | A | 7/2000 | Thompson |
| 6,366,871 | B1 | 4/2002 | Geva |
| 6,434,429 | B1 | 8/2002 | Kraus et al. |

(Continued)

OTHER PUBLICATIONS

Proulx et al., "Development and Evaluation of a Bluetooth EKG Monitoring Sensor", Computer-Based Medical Systems, 2006. CBMS 2006. 19th IEEE International Symposium.

(Continued)

*Primary Examiner* — George Manuel
*Assistant Examiner* — Robert N Wieland
(74) *Attorney, Agent, or Firm* — Pauly, DeVries Smith & Deffner LLC

(57) ABSTRACT

Various embodiments concern a method which may include communicating medical information between a PIMD and an interface module via a first channel in compliance with a predetermined medical information regulatory standard, preventing access to the PIMD via the interface module other than through the first channel, detecting a communication protocol used by an available generic network access device, selecting a communication protocol rule set from a plurality of communication protocol rule sets to effect communication between the interface device and an available generic network access device of a plurality of generic network access devices, and transferring at least some of the medical information to the remote network via a second channel established between the interface module and the available generic network access device using the selected communication protocol rule set.

20 Claims, 11 Drawing Sheets

U.S. PATENT DOCUMENTS

| | | |
|---|---|---|
| 6,546,232 B1 | 4/2003 | Sack et al. |
| 6,574,509 B1 | 6/2003 | Kraus et al. |
| 6,577,901 B2 | 6/2003 | Thompson |
| 6,622,043 B1 | 9/2003 | Kraus et al. |
| 6,665,385 B2 | 12/2003 | Rogers et al. |
| 6,738,671 B2 | 5/2004 | Christophersom |
| 6,781,522 B2 | 8/2004 | Sleva |
| 6,804,558 B2 | 10/2004 | Haller et al. |
| 6,842,645 B2 | 1/2005 | Dalal |
| 6,858,006 B2 | 2/2005 | MacCarter et al. |
| 6,957,107 B2 | 10/2005 | Rogers et al. |
| 6,978,182 B2 | 12/2005 | Mazar et al. |
| 7,009,511 B2 | 3/2006 | Mazar et al. |
| 7,060,030 B2 | 6/2006 | Von Arx et al. |
| 7,127,300 B2 | 10/2006 | Mazar et al. |
| 7,130,396 B2 | 10/2006 | Rogers et al. |
| 7,149,773 B2 | 12/2006 | Haller et al. |
| 7,174,216 B1 | 2/2007 | Dalal |
| 7,181,505 B2 | 2/2007 | Haller et al. |
| 7,203,545 B2 | 4/2007 | Schmitt et al. |
| 7,218,969 B2 | 5/2007 | Vallapureddy |
| 2002/0143595 A1 | 10/2002 | Frank |
| 2002/0158775 A1 | 10/2002 | Wallace |
| 2005/0101841 A9 | 5/2005 | Kaylor et al. |
| 2005/0137480 A1 | 6/2005 | Alt |
| 2005/0245995 A1 | 11/2005 | Diebold |
| 2006/0293607 A1 | 12/2006 | Alt |
| 2007/0049983 A1 | 3/2007 | Freeberg |
| 2007/0049992 A1 | 3/2007 | Freeberg |
| 2007/0053516 A1 | 3/2007 | Katoozi et al. |
| 2007/0083246 A1 | 4/2007 | Mazar et al. |
| 2007/0100396 A1 | 5/2007 | Freeberg |
| 2007/0106433 A1 | 5/2007 | He |
| 2007/0118188 A1 | 5/2007 | Von Arx et al. |
| 2007/0185547 A1 | 8/2007 | Hoyme et al. |
| 2007/0192140 A1 | 8/2007 | Gropper |
| 2007/0195163 A1 | 8/2007 | Chestak et al. |
| 2007/0299317 A1 | 12/2007 | Hoyme et al. |
| 2008/0004904 A1* | 1/2008 | Tran .................................. 705/2 |
| 2008/0139891 A1 | 6/2008 | Whitehead |
| 2008/0215360 A1 | 9/2008 | Dicks |
| 2008/0218376 A1 | 9/2008 | Dicks |
| 2009/0058635 A1 | 3/2009 | LaLonde |
| 2009/0058636 A1 | 3/2009 | Gaskill |
| 2009/0062887 A1 | 3/2009 | Mass |
| 2009/0063187 A1 | 3/2009 | Johnson |
| 2009/0063193 A1 | 3/2009 | Barton |

OTHER PUBLICATIONS

Jasemain et al., "Evaluation of a realtime, remote monitoring telemedicine system using the Bluetooth protocol and a mobile phone network", J. Telemed Telecare, vol. 11, Issue 5, 2005, pp. 256-260.

Gouaux et al., Pervasive self-card solutions in telecardiology, Stud Health Technol Inform, 2003, pp. 119-124.

Webb, "EDN hands-on project: Mobile Makeover", EDN, 2006.

Sivaraman et al., "Optimizing handsets' multimedia connectivity and performance", EDN, 2007.

File History for U.S. Appl. No. 12/435,866 as retrieved from the U.S. Patent and Trademark Office System on Jan. 24, 2012, 187 pages.

File History for U.S. Appl. No. 13/357,399 as retrieved from the U.S. Patent and Trademark Office System on Sep. 11, 2012, 137 pages.

* cited by examiner

REGULATORY COMPLIANT TRANSMISSION OF MEDICAL DATA EMPLOYING A PATIENT IMPLANTABLE MEDICAL DEVICE AND A GENERIC NETWORK ACCESS DEVICE

RELATED APPLICATIONS

This application is a continuation of U.S. patent application Ser. No. 13/357,399, filed on Jan. 24, 2012, now U.S. Pat. No. 8,265,757, which is a continuation of U.S. patent application Ser. No. 12/435,866, filed on May 5, 2009, now U.S. Pat. No. 8,103,346, which claims the benefit of Provisional Patent Application Ser. No. 61/128,583, filed on May 22, 2008, to which priority is claimed pursuant to 35 U.S.C. §120 and 35 U.S.C. §119(e), respectively, and which are hereby incorporated herein by reference in their entireties.

FIELD OF THE INVENTION

The present invention relates generally to communicative medical devices, and more specifically, to regulatory compliant transmission of medical data from a patient implantable medical device to a remote server using a generic network access device.

BACKGROUND

Implantable pulse generators (IPGs) are commonly used to treat irregular heartbeats, known as arrhythmias. Cardiac pacemakers, for example, are designed to manage bradycardia, an abnormally slow or irregular heartbeat. Left untreated, bradycardia can cause symptoms such as fatigue, dizziness, and fainting. Cardiac resynchronizers are a particular class of pacemaker that provide cardiac resynchronization therapy, such a bi-ventricular pacing, for patients suffering from heart failure. Implantable cardioverter defibrillators (ICDs), by way of further example, are designed to treat tachycardia, heart rhythms that are abnormally fast and life threatening. Some forms of tachycardia can result in sudden cardiac death, if left untreated. The IPG 110 illustrated in FIG. 1, shown coupled to a heart 120, is one example of a variety of patient implantable medical devices (PIMD) used to gather data and/or deliver a therapy, such as a cardiac therapy.

PIMD's are increasingly being equipped with an on-board, volatile memory in which telemetered signals can be stored for later retrieval and analysis. The telemetered signals provide various types of patient device information, such as atrial electrical activity, ventricular electrical activity, time of day, activity level, cardiac output, oxygen level, cardiovascular pressure measures, pulmonary measures, and any interventions made on a per heartbeat or binned average basis. In addition, a growing class of cardiac medical devices, including implantable heart failure monitors, implantable event monitors, cardiovascular monitors, and therapy devices, are being used to provide similar stored device information. These devices are typically designed to store approximately thirty minutes of heartbeat data. Telemetered signals are also stored in a broader class of monitors and therapeutic PIMD's for other areas of medicine, including metabolism, endocrinology, hematology, neurology, muscular, gastrointestinal, genital-urology, ocular, auditory, and the like.

Information stored in a PIMD is typically retrieved using a proprietary interrogator or programmer, often during a clinic visit or following a device event. The volume of data retrieved from a single device interrogation procedure can be large and proper interpretation and analysis can require significant physician time and detailed subspecialty knowledge, particularly by cardiologists and cardiac electrophysiologists. Present approaches to data interpretation and understanding, and practical limitations on time and physician availability, make such analyses impracticable.

Conventional systems for collecting and analyzing pacemaker and ICD telemetered signals in a clinical or office setting can be used to retrieve data, such as patient electrocardiogram and any measured physiological conditions, collected by the IPG for recordation, display, and printing. The retrieved data may be displayed in chronological order and analyzed by a physician. Conventional systems often lack remote communications facilities and must be operated with the patient present. These systems present a limited analysis of the collected data based on a single device interrogation and lack the capability to recognize trends in the data spanning multiple episodes over time or relative to a disease specific peer group.

SUMMARY OF THE INVENTION

The present invention is generally directed to systems and methods for regulatory compliant transmission of medical data employing a patient implantable medical device and a generic network access device.

Various embodiments of the invention concern the collection of medical information, such as electrocardiograms, from a patient implantable medical device. The information can be transferred to a remote server across a public network in a manner compliant with regulatory and other standards regarding the transmission of medical information. The transfer is facilitated by an interface device in communication with a generic network access device.

According to various embodiments, an interface module for facilitating communication and data transmission between a PIMD and any one of a plurality of generic network access devices with a remote server via a public network in accordance with a plurality of disparate communication protocols can be used. The interface module can include first circuitry comprising a first communications interface configured for communication with a PIMD, and a regulatory compliance module having an input coupled to the first communications interface, an output, and a regulatory memory for storing compliance rules consistent with a predetermined medical device regulatory requirements specification, the compliance module configured to moderate communicative interaction between the PIMD and the first circuitry and to process PIMD data in accordance with the compliance rules. The interface module can further include second circuitry having an input coupled to the output of the compliance module, the second circuitry including a protocol library comprising sets of communication protocol rules, each communication protocol rule set associated with one of a plurality of disparate communication protocols, and a second communications interface coupled to the protocol library and configurable to implement any one of the communication protocol rule sets, the first communications circuitry partitioned from the second communications circuitry such that the PIMD data is communicated to the input of the second circuitry only via the output of the compliance module. The interface module can include a processor coupled to the first and second circuitry, the processor configured to detect a communication protocol used by an available generic network access device of a plurality of generic network access devices and select a communication protocol rule set from the protocol library for implementation by the second communications interface to effect communication between the interface module and the available generic network access device. The interface module can include a housing configured to house the first communication circuitry, the second communication circuitry, and the processor.

In such embodiments, at least some of the plurality of generic network access devices, including the available generic network access device, can comprise one of a plurality of different cellular telephones each using a different one of the plurality of disparate communication protocols, and the interface device is configured to facilitate transmission of PIMD data in compliance with the predetermined medical device regulatory requirements specification between the PIMD and the remote service via the public network using any one of the plurality of different cellular telephones without being reconfigured to facilitate transmission of PIMD data in compliance with the predetermined medical device regulatory requirements specification when switching use of different ones of the plurality of different cellular telephones.

According to various embodiments, a method can be implemented by use of an interface module transportable by an ambulatory patient for facilitating transfer of medical information between a PIMD and a remote network server using any one of a plurality of generic network access devices having disparate communication protocols. Such a method can include communicating medical information between the PIMD and the interface module via a first channel and in compliance with a predetermined medical information regulatory standard. Such a method can include preventing access to the PIMD via the interface module other than through the first channel. Such a method can include detecting a communication protocol used by an available generic network access device. Such a method can include selecting a communication protocol rule set from a plurality of communication protocol rule sets to effect communication between the interface device and an available generic network access device of a plurality of generic network access devices, each of the protocol rule sets associated with one of the disparate communication protocols. Such a method can include transferring at least some of the medical information to the remote network via a second channel established between the interface module and the available generic network access device using the selected communication protocol rule set, wherein the at least some of the medical information is transferred between the interface device and the remote network in compliance with the predetermined medical information regulatory standard.

Such a method can further include detecting an additional communication protocol used by an additional generic network access device of the plurality of generic network access devices, selecting an additional communication protocol rule set from the plurality of communication protocol rule sets to effect communication between the interface device and the additional generic network access device, and transferring at least some of the medical information to the remote network via a third channel established between the interface module and the additional generic network device using the selected additional communication protocol rule set, wherein the at least some of the medical information is transferred between the interface device and the remote network in compliance with the predetermined medical information regulatory standard.

According to various embodiments, an interface device for facilitating transfer of medical information between a PIMD and a remote network server via a public network using any one of a plurality of generic network access devices having disparate communication protocols can be provided. The interface device can include a portable housing configured for transport by an ambulatory patient, first communication circuitry configured to implement medical firmware to effect communication between a PIMD and the interface device in compliance with a predetermined medical information regulatory standard, second communication circuitry configured to implement communication firmware to effect communication between the interface device and any one of a plurality of generic network access devices, memory configured to store a plurality of communication protocol rule sets, each communication protocol rule set associated with a communication protocol of a different one of the plurality of generic network devices, a processor coupled to the memory and the first and second communication circuitry, the processor configured to detect a communication protocol used by an available generic network access device of the plurality of generic network access devices and select a communication protocol rule set from memory for implementation by the second communication circuitry to effect communication between the interface device and the available generic network device, and a power source configured to supply power to components of the interface device, the power source, memory, processor, and first and second communication circuitry supported by the housing, wherein each of the plurality of generic network access devices is agnostic with respect to compliance protocol associated with the predetermined medical information regulatory standard.

According to various embodiments, a system for transferring medical information between a PIMD and a remote server over a public network using an interface module and any one of a plurality of generic network access devices. The system can include means for communicating medical information between the PIMD and the interface module via a first channel and in compliance with a predetermined medical information regulatory standard. The system can also include means for preventing access to the PIMD via the interface module other than through the first channel. The system can also include means for detecting a communication protocol used by an available generic network access device. The system can also include means for selecting a communication protocol rule set from a plurality of communication protocol rule sets to effect communication between the interface device and an available generic network access device of a plurality of generic network access devices, each of the protocol rule sets associated with one of the disparate communication protocols. The system can also include means for transferring at least some of the medical information to the remote network via a second channel established between the interface module and the available generic network access device using the selected communication protocol rule set, wherein the at least some of the medical information is transferred between the interface device and the remote network in compliance with the predetermined medical information regulatory standard.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
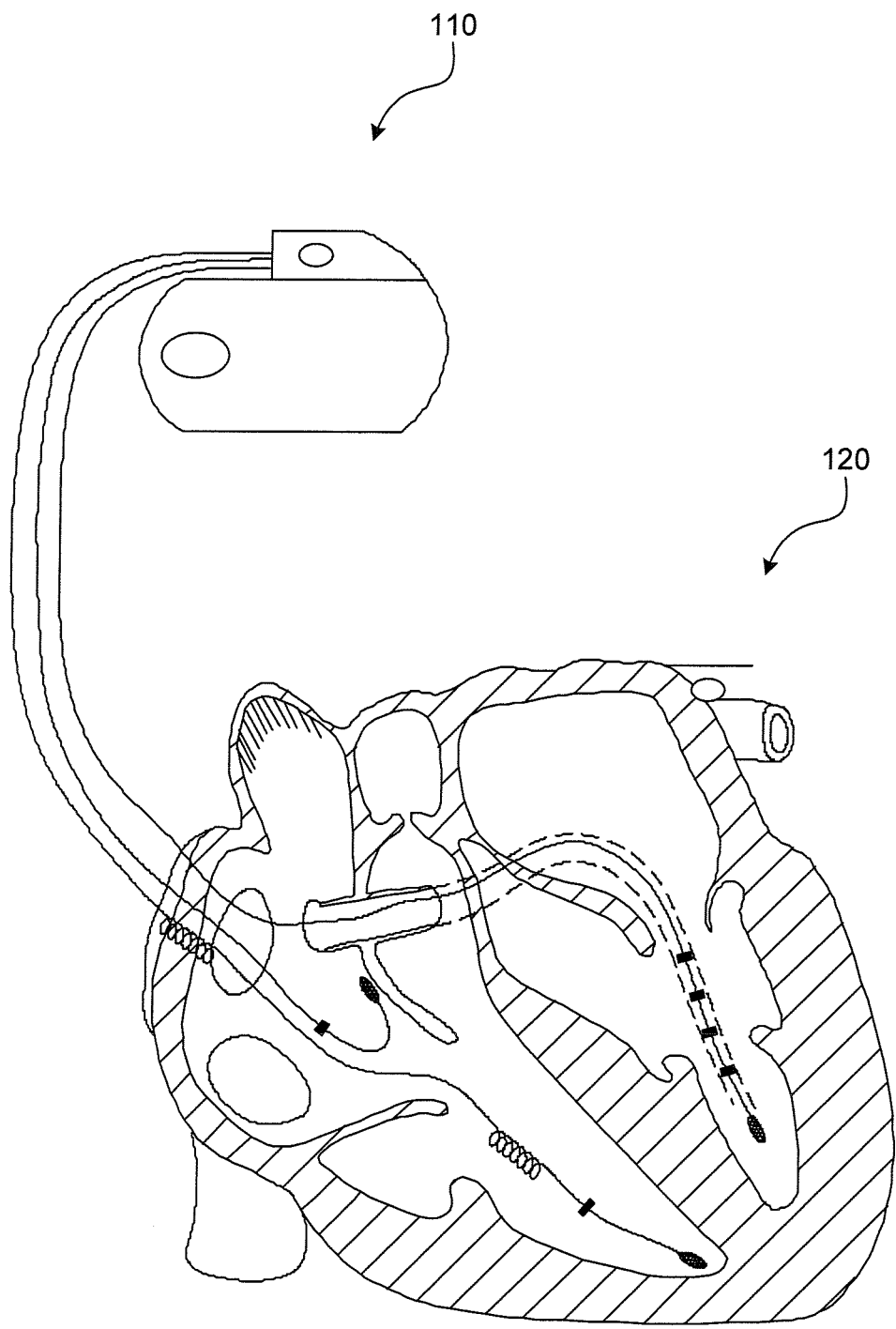
FIG. 1 illustrates a patient-implantable device that may be used in conjunction with medical data transmission methodology in accordance with various embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

The discussion and illustrations provided herein are presented in an exemplary format, wherein selected embodiments are described and illustrated to present the various aspects of the present invention. Systems, devices, or methods according to the present invention may include one or more of the features, structures, methods, or combinations thereof described herein. For example, a device or system may be implemented to include one or more of the advantageous features and/or processes described below. A device or system according to the present invention may be implemented to include multiple features and/or aspects illustrated and/or discussed in separate examples and/or illustrations. It is intended that such a device or system need not include all of the features described herein, but may be implemented to include selected features that provide for useful structures, systems, and/or functionality.

One advantageous aspect of PIMD's is their convenience in collecting data and ability to be constantly monitoring for, and poised to therapeutically address, conditions necessitating therapy delivery. A patient with an ICD can, for example, be outside of a hospital or other clinical environment while the ICD implantably collects data and delivers cardiac therapy when warranted. Health care professionals are generally interested in the data collected by the ICD as well as information regarding any therapies delivered by the ICD. Moreover, health care professionals may also be interested in modifying operation of an ICD, such as, for example, the manner in which data is collected, stored, and therapy is triggered and delivered. Remote access to a PIMD further extends the convenience of a PIMD for both the patient and health care professionals, allowing for the collection of data and modification of device operation without a hospital visit.

Remote server acquisition of a patient's physiologic data may occur while the patient is ambulatory, such as during daily routines at the home or office, or when traveling locally, nationally, or worldwide. Physiologic data for patients may be acquired by a wide variety of sensors, including external and internal sensors. For example, a PIMD may acquire physiologic data and transmit such data to a server via a generic network access device (e.g., an off-the-shelf cellular telephone configured for general communications and not configured to comply with regulatory standards for handling medical information) and an interface module (e.g., an interface device (IFD)), the interface module facilitating information transfer between the PIMD and the generic network access device, as will be discussed further herein. As used herein, generic network access devices refers to publicly available devices configured to connect with network infrastructure and facilitate the transfer of information across a network that are not specially designed, manufactured, certified, configured, or programmed to transfer medical information in a manner compliant with regulatory standards for handling medical information. Generic network access devices, as referred to herein, can include cellular telephones, pagers, personal digital assistants (PDA's), and the like. For example, element 15, illustrated in FIG. 2 and elsewhere herein, is such a generic network access device.

Data acquired by a PIMD may be transmitted to a remote server in real-time, such as by use of a real-time data streaming protocol. Store and forward data transfer protocols may also be employed, such as for less critical data. Incremental data transfers may also be performed to reduce the volume of data transferred from intermediary devices to the remote server.

Transfer of patient physiologic data may be triggered by clinical events detected by a sensor and/or patient implantable medical device provided with the patient. Data transfers may also be triggered in accordance with query/response protocols and/or periodic schedules.

Examples of patient data that may be transferred from a PIMD to a remote server via an IFD include electrograms (EGMs), clinical event data, episode counters, alerts, device or sensor settings, battery status, lead measurements, and patient activity level, among other types of data. Data transferred from an IFD to a remote server using a generic network access device may be integrated at a web site supported by the remote server and displayed at a remote location (e.g., physician's office).

Transmission of data across and between networks, including wireless networks, is widely practiced. However, special considerations must be made when transmitting medical data, especially across wireless and public networks. For example, medical data often contains sensitive and private information. Compliance with the Health Insurance Portability and Accountability Act (HIPPA) and other laws and regulations can require special procedures for handling of medical data.

In addition, it can be especially important that the transmission of medical data takes place at an appropriate time. For example, a PIMD may detect a dangerous medical condition requiring intervention, and in such a case a PIMD may need immediate access to a network to communicate information regarding detection of the condition to appropriate health care processionals. Moreover, unlike most data, the accurate and prompt transmission of medical data can become a life and death matter.

Accounting for these considerations often results in the various network components used for medical data transmission being configured to function as medical devices, as they are especially configured to manage the sensitive nature of medical information as discussed above. Such medical devices may be designed and manufactured for robustness and reliability to ensure reliable and accurate data transfer, design considerations which often come at the price of less portability and with increased device costs. As such, special equipment must be especially designed, manufactured, and certified by a regulatory agency to facilitate the transmission of medical information. For example, a cellular telephone may be specially configured to receive medical information directly, or indirectly through a relay device, from a PIMD, and transmit the medical information through a mobile network (e.g., a GSM network) to a server for analysis. In such a case, the cellular telephone must be specially configured to handle the medical information such that the cellular telephone is certified by the Food and Drug Administration (FDA) as a Class III medical device. This raises the development, manufacturing, and operating costs associated with medical treatment. Additionally, such specialty equipment cannot be easily replaced if it is damaged, lost, or if a patient travels through an area that does not support the particular transmission protocol (e.g., GSM) of the configured network access device.

It may be unnecessary, impractical, or otherwise undesirable to restrict patients to physical areas where specially regulated and certified medical equipment is located to facilitate information communication with patient management services. In many cases the patient's condition or health does not restrict the patient from normal daily activities, or at least from activities that would separate the patient from fixed equipment and/or a service region used to communicate with patient management services.

Solutions provided by the invention enhance patient mobility by enabling wireless communication of data, commands, and/or other information between patient devices and patient management systems using generic network access devices. By furnishing the patient with such mobile and replaceable capabilities, communication can be effected periodically or continuously, at any needed time or place (e.g., locally, nationally, or worldwide) while reducing costs, specialized equipment, and inconvenience for the patient.

Embodiments of the present invention address these and other issues by providing an interface device (IFD) for facilitating data transmission between a PIMD and a remote server using any one of a variety of generic network access devices while complying with regulatory standards for handling medical information.

Figure 2:
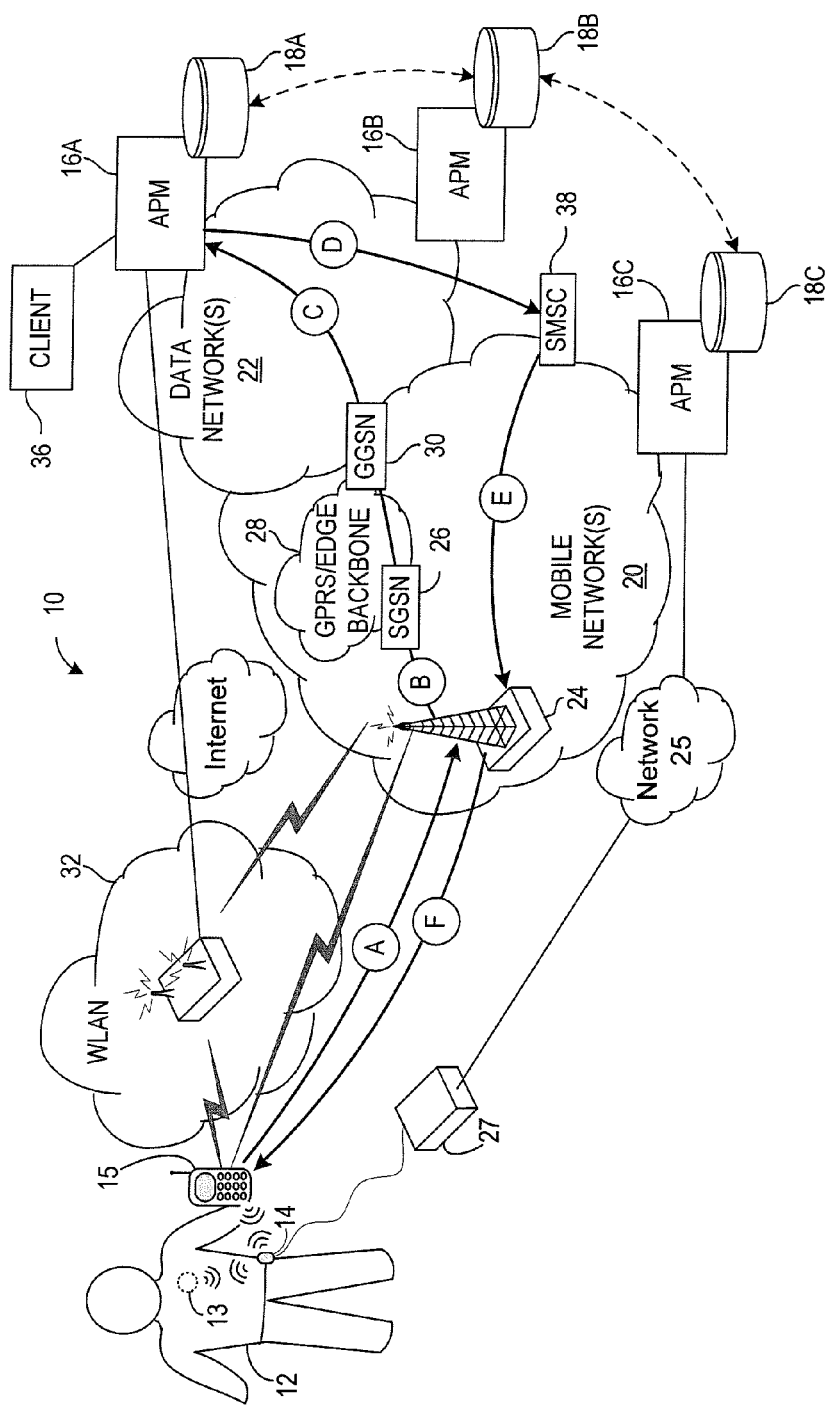
FIG. 2 is a diagram illustrating a data transmission across various networks in accordance with various embodiments of the present invention.

FIG. 2 illustrates an exemplary automated or advanced patient management environment 10 supported by the present invention. Patient 12 is associated with one or more data sources or medical devices (hereinafter medical devices) associated with that patient 12. These medical devices include, for example, a PIMD 13 that delivers or provides therapy to the patient 12, medical sensors that sense physiological data in relation to the patient 12, and/or measurement devices that measure environmental parameters occurring independent of the patient 12.

Each patient medical device can generate one or more types of patient data and can incorporate one or more components for delivering therapy, sensing physiological data and measuring environmental parameters. Representative medical devices include PIMD's such as pacemakers, implantable cardiac defibrillators, drug pumps, neuro-stimulators and the like. External medical devices may similarly provide medical information for transmission, such as automatic external defibrillators (AEDs), drug delivery systems, pill dispensers, respiratory therapy systems (e.g., using CPAP devices), among others. The medical devices may also include implantable or external sensors. Implantable sensors include, for example, heart and respiratory monitors, implantable diagnostic multi-sensor non-therapeutic devices, etc. External sensors may include Holter monitors, weight scales, blood pressure cuffs, pulse oximeters, glucose monitors, etc. Other types of medical, sensing, and measuring devices, both implantable and external, are possible.

The patient 12 involved with the advanced patient management environment is also associated with at least one IFD 14 capable of communicating with a wireless network, such as one providing access to an advanced patient management (APM) system represented by one or more APM servers 16A, 16B, 16C. Each APM server may include a database 18A, 18B, 18C to store information such as patient data. The APM server arrangement may be implemented in a single server/database 16A/18A, or may include multiple servers and databases as depicted in FIG. 2. Further, the APM server arrangement may include multiple servers and associated databases operating substantially independently. In such a case, information may be exchanged between any of the APM servers through information requests and responses. Alternatively, multiple servers and databases may operate as a distributed server/database system to collectively serve as a single APM system.

A cellular network generally refers to a radio network made up of numerous cells generally defined by a transmitter or "base station." Each base station provides coverage for an area defining its respective cell, and the collective cell structure thus provides radio coverage over a wider area. The mobile network(s) 20 may represent any one or more known or future wireless networking technologies, such as the Global System for Mobile Communications (GSM), Universal Mobile Telecommunications System (UMTS), Personal Communications Service (PCS), Time Division Multiple Access (TDMA), Code Division Multiple Access (CDMA), Wideband CDMA (WCDMA), and/or other mobile network transmission technologies.

In one embodiment of the invention, the patient's 12 IFD 14 communicates wirelessly through a GSM network using a generic network access device 15 to gain access to the GSM based network. Data may be communicated via a General Packet Radio System (GPRS) mobile communications network, where GPRS refers to a packet-switched service for GSM that mirrors the Internet model and enables seamless transition towards advanced generation networks. GSM/GPRS networks have further evolved to provide increased data transfer rates over the network. For example, one embodiment of the invention exploits the Enhanced Data rates for GSM Evolution (EDGE), which is also known as Enhanced GPRS (EGPRS). EDGE is a digital mobile technology that allows for increased data transmission rates and reliability, and is essentially a "bolt on" enhancement to second generation GSM and GPRS networks. Further enhancements to EDGE networks, such as "EDGE Evolution," provides even further increases in data rates, error correction and signal quality.

Data communicated between the IFD 14 and the mobile network(s) 20 via the generic network access device 15 is ultimately communicated to or from the APM 16A. As previously indicated, the APM 16A may or may not be associated with one or more other discrete or distributed server/database systems 16B/18B, 16C/18C, etc. One or more data networks 22 may cooperatively operate with the mobile network(s) 20 to facilitate data transfers to and from the relevant APM 16A. For example, the illustrated data network 22 may represent the Internet, which interfaces to the illustrated EDGE or other mobile network 20 to serve landline APM 16A systems.

The IFD 14 may communicate with a base station 24 via generic network access device 15. The base station 24 represents a component of the wireless network access infrastructure that terminates the air interface over which subscriber traffic is communicated to and from the IFD 14 via the generic network access device 15. A Base Station Controller (BSC) (not shown) is a switching module that provides, among other things, handoff functions, and controls power levels in each base station. The BSC controls the interface between a Mobile Switching Center (MSC) (not shown) and base station 24 in a GSM/GPRS or EDGE mobile network 20, and thus controls one or more base stations 24 in the set-up functions, signaling, and in the use of radio channels.

A BSC also controls the interface between the Serving GPRS Support Node (SGSN) 26 and the base station 24 in such a mobile network 20. The SGSN 26 serves, for example, a GPRS or EDGE-equipped mobile by sending or receiving packets via the base station 24 at the mobile interface of the GPRS/EDGE backbone network 28. The SGSN 26 can manage the delivery of data packets to and from the IFD 14 and/or generic network access device 15 within its service area, and performs packet routing and transfer, mobility management, logical link management, billing functions, etc. In the exemplary GPRS/EDGE embodiment shown in FIG. 2, the location register of the SGSN 26 can store location information such as the current generic network access device 15 (in this figure illustrated as a cellular telephone) and Visiting Location Register (not shown) associated with the IFD 14, as well as user profiles such as the International Mobile Subscriber Identity Number (IMSI) of all users registered with this SGSN 26.

Another network element introduced in the GPRS/EDGE context is the Gateway GPRS Support Node (GGSN) 30, which acts as a gateway between the GPRS/EDGE backbone network 28 and a data network(s) 22. For example, the GGSN 30 may serve as a gateway between the GPRS/EDGE backbone network 28 and the Internet, or other data networks such as an Internet Protocol (IP) Multimedia Core associated with IP multimedia subsystems (IMS). The GGSN 30 allows mobile devices, such as the IFD 14, to access the data network 22 or specified private IP networks. The connection between the GGSN 30 and the data network 22 is generally enabled through a standard protocol, such as the Internet Protocol (IP). IP or other network protocol can be used to facilitate a connection between the IFD 14 and APM 16C via router 27 and network 25.

In the illustrated example involving an EDGE or other GSM-based network, data from the PIMD 13 is transmitted to IFD 14 using, for example, RF or inductance based technologies. The data can then be relayed through the generic network access device 15 using functions of the IFD 14 to the base station 24 (relay "A"), and forwarded (relay "B") to the SGSN 26 and GGSN 30 for delivery (relay "C") via the data network 22 to the targeted APM server 16A. The IFD 14 may alternatively or additionally communicate via a proximity network(s) 32 such as a wireless local area network (WLAN). For example, where the IFD 14 is within a transmission range of a WLAN (e.g., IEEE 802.11b/g network), the IFD 14 can be configured to automatically or manually connect to the WLAN 32. Other proximity networks 32 can also be employed, such as Bluetooth, Zigbee, and/or WIMAX, among others. Such proximity networks can address connectivity issues with the mobile network 20, such as within a building where reception can be less than optimal.

In certain configurations, networks are described herein in terms of node networks, although arrangement of the networks as mesh networks is equally applicable to some aspects of the present invention.

The data transmitted by the IFD 14 may be stored and/or analyzed at the APM 16A, which may be further coupled to one or more client stations 36 to perform input and output functions. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The mobile network 20 can further facilitate data or command transfer from the APM 16A to the IFD 14 and further to a medical device, such as PIMD 13. Data can be transferred in reverse sequence ("C," "B," "A"). Other channels may additionally or alternatively be used. For example, one embodiment involves sending commands from the APM 16A to the IFD 14 using messaging services supported by the mobile network 20 and data network 22 infrastructures. These messaging services include, for example, Short Message Service (SMS), Enhanced Messaging Service (EMS), Multimedia Messaging Service (MMS), etc. These messaging technologies represent "store-and-forward" message services. For example, the APM 16A may send "D" an SMS message that is received by an SMS Center (SMSC) 38 that provides the store-and-forward functionality, and is responsible for delivering message(s) (relay "E") to the base station 24 for ultimate delivery to the address of the targeted IFD 14 (relay "F"). The SMSC 38 stores the message until the IFD 14 is available, at which time it forwards the message, removes it from the SMSC 38, and notifies the APM 16A that the message has been forwarded. Issuing commands from the APM 16A to the IFD 14 using SMS is described more fully below.

MMS, also based on the store-and-forward service model, is similar to SMS in the manner that messages are communicated. However, unlike SMS, MMS is not limited to text messages. The destination address used in an MMS message may be the recipient's public number such as the Mobile Station Integrated Services Digital Network Number (MSISDN), or may be an e-mail address. Therefore, to minimize the chance of the IFD 14 receiving an SMS from an inadvertent source, a lengthy or otherwise unique e-mail address can be contrived and used as the destination address at the IFD 14. To minimize the risk of misdirected messages, messaging techniques such as those described herein may be combined with cryptographic authentication mechanisms to ensure that the IFD 14 doesn't attempt to process and erroneous message.

It should be recognized that the present invention may utilize mobile networks 20 other than GSM-based systems. For example, the Universal Mobile Telecommunications System (UMTS) is a 3G mobile technology that may in the future, and in some instances currently, replace GSM/GPRS network infrastructures. UMTS has a different air interface than GSM that can be connected to different backbone networks such as the Internet, ISDN, GSM or other UMTS networks. The IFD 14 can be configured to communicate via a UMTS network or any other existing or future network.

Figure 3:
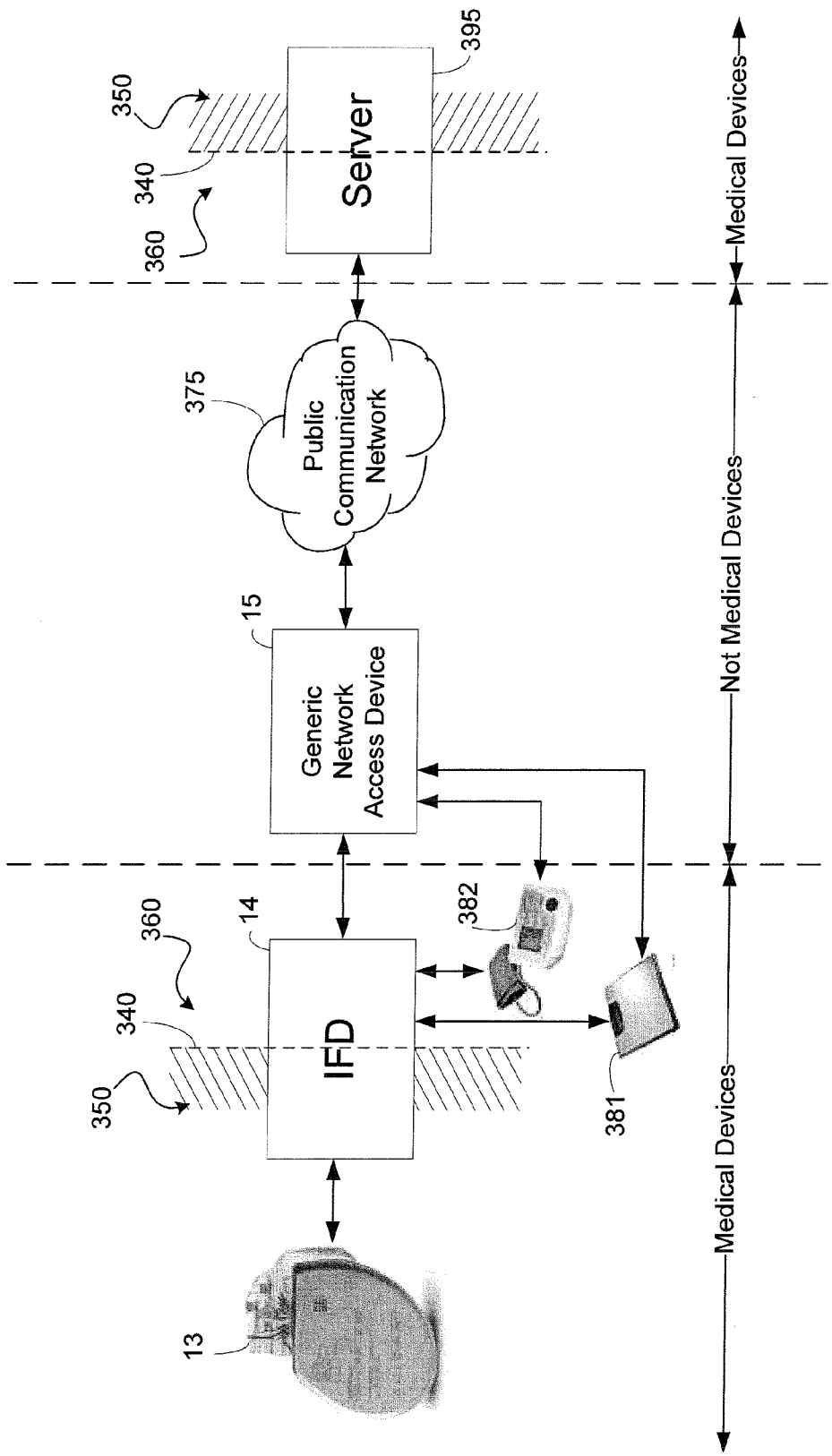
FIG. 3 is a diagram illustrating medical data transmission from a patient implantable medical device to a server in accordance with various embodiments of the present invention.

Various embodiments of the invention are configured to operate on multiple mobile networks and/or through multiple data transmission channels while complying with regulatory standards controlling the handling of medical information. The ability to operate on multiple networks and/or through multiple data transmission channels increases the flexibility and ease of use of a communication system. For example, a particular cellular telephone using UMTS may not be compatible with GSM. As depicted in FIG. 3, the IFD 14 is configured as a multi-mode device capable of switching between disparate network infrastructures, such as an EDGE network and a UMTS network. If a patient equipped with an IFD 14 travels to an area without a first network coverage, the IFD 14 can switch to an alternative network, the alternative network being one of a variety of networks, communication infrastructures, and communication schemes that can be utilized by the IFD 14 to facilitate communication between a PIMD 13 and a remote server.

An IFD of the present invention can be programmed with a variety of communication protocols for communicating using different networks that use different communication protocols. Such a feature allows the IFD to match a particular protocol used in a particular locale, country, or worldwide corresponding to the particular generic network access device being used to connect to the network. The IFD can then switch protocols when needed to maintain connectivity when the patient moves from one network coverage area to another and/or switches use from one generic network access device that facilitates connectivity to another generic network access device.

For example, a patient's IFD 14 may ordinarily communicate data with the APM 16A via a GSM/EDGE network. If the patient moves to an area having only UMTS coverage, the IFD 14 can switch to a UMTS network by use of a generic network access device compatible with a UTMS network. Determination of which network is available can be accomplished in various manners, including determining what country or region the IFD 14 is in based upon the base station signal and/or scans performed by an IFD 14 to determine what generic network access devices and respective functionalities are available for use.

A PIMD 13 may communicate with the IFD 14 via various communication channels. A PIMD 13 or other medical device may communicate using the Medical Implant Communication Service (MICS), which is a reserved frequency band between 402-405 MHz. Other frequency bands may alternatively be used, such as the Industrial, Scientific and Medical (ISM) radio band, the Short Range Devices (SRD) radio band or others.

A PIMD 13 of the present invention may be configured to operate in the ISM and/or MICS frequency bands, or in other channels. A PIMD of the present invention may include a configurable transceiver module (e.g., software defined radio (SDR)), or provide multiple transceiver modules respectively associated with each of the ISM or MICS (and/or other) frequency bands. The desired band may be designated through remote commands from the APM 16A or elsewhere. The PIMD 13 may also be configured to automatically switch between communication channels in response to a triggering event. For example, communication between a PIMD 13 and the IFD 14 may switch from MICS to ISM if the MICS transceiver circuitry fails, thereby providing redundancy. The IFD 14 may be configurable in a like manner. For example, the IFD 14 may automatically recognize the frequency of the signal and implement the appropriate ISM, MICS, or other circuitry.

Devices equipped with sensors, such as PIMD 13, acquire the data that is ultimately communicated to the APM 16A. This data varies depending on the type of medical device involved. In the case of PIMD's, examples of the acquired and communicated data include electrograms (EGM), events, episode counters, alerts, device settings, battery status, lead measurements, patient activity level, and the like. Data may be provided to comply with electronic medical record (EMR) standards. Collected data may be transferred all at once, or incrementally. Requests for data may also include data accumulated over time, such as certain data occurring on a daily, weekly, monthly, or other duration basis. The APM 16A may selectively request, by way of the IFD 14, particular portions of the data stored in the PIMD 13 or other medical device.

Some IFD's are capable of communicating with APM 16A at any time, and thus provide an "always connectable" functionality, assuming a connection is available. In addition to scheduled data transfers, this "always connectable" functionality supports event-driven data transfers that are provided in response to an event. Such events may be based on data analysis results, date, time of day, monitored conditions, etc. For example, if a particular patient-related health event occurs, relevant data can be immediately transmitted to the APM 16A via the IFD 14. Communication of data between the various components may be customized for enhanced operation. Systems and methods involving customized data collection for a medical device which may be useful in combination with the embodiments described herein are provided in commonly owned U.S. Patent Application Publication No. 2007/0299317, which is incorporated herein by reference. Subject matter which may be useful in light of the present disclosure is disclosed in U.S. Patent Application Publication Nos. 2009/0058635, 2009/0058636, 2009/0062887, 2009/0063187, and 2009/0063193, which are incorporated herein by reference.

Other examples relate to PIMD 13 diagnostic or operating conditions. One example is a low PIMD 13 battery condition, which can be sent upon its recognition. Another example is an early memory overwrite warning where a notification can be transmitted when the PIMD 13 memory is at a particular capacity level (e.g., 90%). Yet another example is emergency ambulatory communication of critical patient data. The notification can be used to trigger an interrogation of the PIMD 13 to retrieve the stored data.

In one embodiment, the IFD 14 receives and/or transmits device-independent data. Consequently the IFD 14 can operate with different types or models of PIMD's or other medical devices. This can be accomplished by configuring the IFD 14 according to the particular type of PIMD 13 to which the communicator is, or will be, paired. When interrogating the PIMD 13, the IFD 14 can send or forward generic commands such as "send episodes 1-3." This could be in the form of, for example, a style sheet. Alternatively, the communicator can convert data from any type/model of PIMD 13 to a common data structure. Data can also be compressed, either in the PIMD 13 or the IFD 14, or both.

FIG. 3 demonstrates, among other things, the transfer of medical information between a PIMD 13 and a private server 395 through a public communication network 375 by use of an IFD 14 and a generic network access device 15 according to the present invention. For example, the PIMD 13 can wirelessly send data to, and receive data from, the IFD 14. The data may be transferred between the PIMD 13 and the IFD 14 using inductance and/or RF based communication (e.g., Bluetooth or other PAN protocol), among other communication methods. In this way, an IFD 14 can function as an information buffer for transfer of the data across a network using one or more generic network access devices 15 to a private server 395 or other destination.

As discussed herein, PIMD 13 can transmit data to the IFD 14, wherein the IFD 14 conditions the data for transmission across a public communication network 375 to a private server 395 using a generic network access device 14. As will be discussed further below, a partition 340 is created to separate a public side 360 from a private side 350.

According to some embodiments, medical data is conditioned on the private side 350 of the partition 340 before the medical data is transmitted through the public side 360 using a generic network access device 15. Because of the conditioning of the medical data on the private side 350 of the partition 340, the devices that facilitate transmission of the medical data between the IFD 14 and the server 395 do not need to be specially configured and/or certified as medical devices to handle sensitive medical data and comply with transmission standards (e.g., they are agnostic with respect to the medical regulatory standards). The IFD 14 and the server 395 perform functions on both sides of the partition 340, and therefore must be specifically configured to handle medical information to comply with medical regulatory standards. Because PIMD 13, IFD 14, and server 395 are specifically configured to comply with standards concerning the handling and transmission of medical information, they are medical devices.

Scale 381 and blood pressure device 382 are both medical devices, as they are specifically configured to collect, handle, and transmit medical information in a manner complaint with regulatory standards regarding medical information. Each of the scale 381 and the blood pressure device 382 have multiple channels available to communicate with server 395. For example, the scale 381 and blood pressure device 382 can communicate directly with the IFD 14 and/or the generic network access device 15, as will be explained herein below.

Although FIG. 3 illustrates a scale 381 and blood pressure device 382, many other sensor based devices can be likewise used for the collection and transmission of medical information. Such sensors include, but are not limited to, a posture sensor, a motion sensor, an activity sensor, a step counter, a pedometer, a pulse oximeter, a photoplethysmography sensor, a fat or fluid change sensing arrangement, a respiratory sensor, optical or photonic blood chemistry sensors, and a temperature sensor, among others.

FIG. 3 can represent the same embodiment represented in the other Figures, such as FIGS. 1, 2, 4, and 5, with various aspects emphasized and deemphasized.

Figure 4:
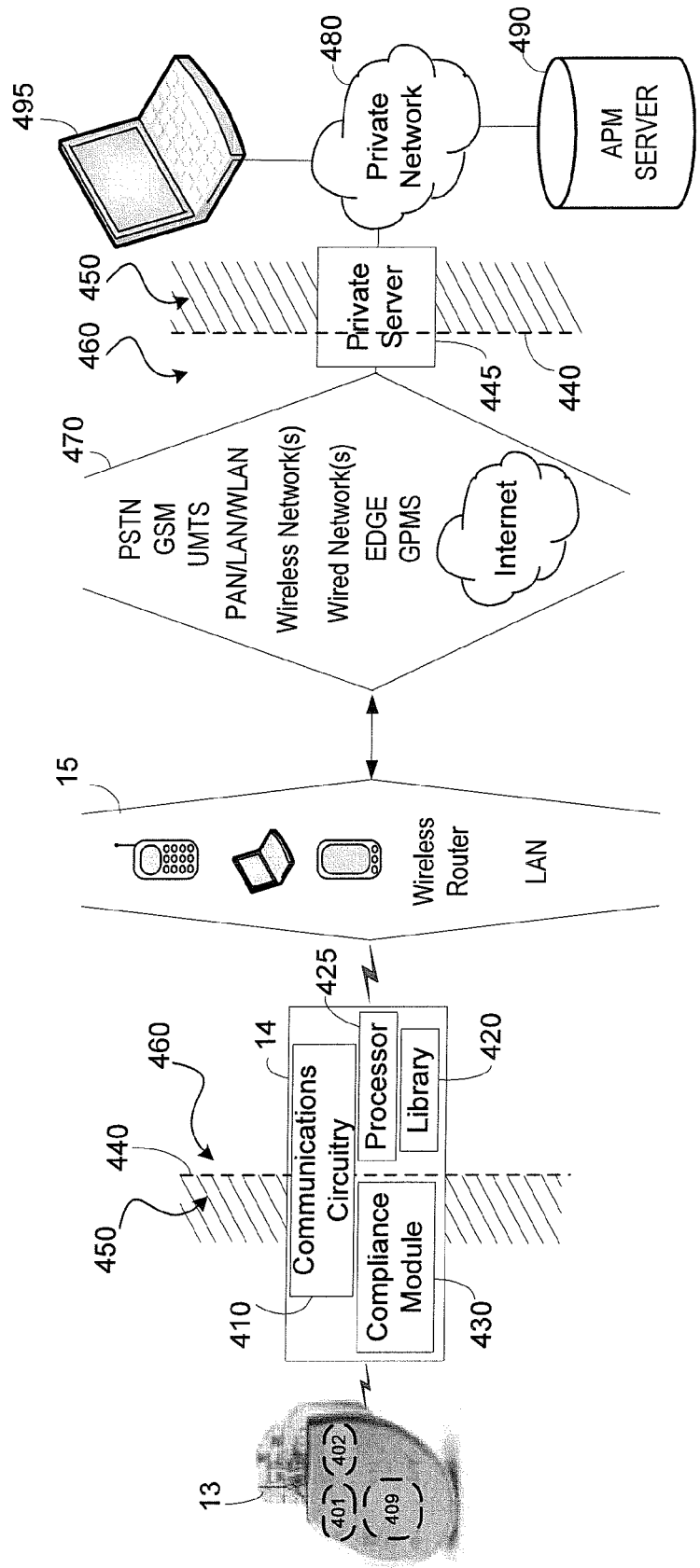
FIG. 4 is a diagram illustrating medical data transmission from a patient implantable medical device to a private network using various generic network access devices and protocols in accordance with various embodiments of the present invention.

FIG. 4 demonstrates, among other things, the flexibility and security provided in communication between a PIMD 13 and an APM server 490 by use of an IFD 14 according to the present invention. Transfer of data between the PIMD 13 and the APM server 490 via IFD 14 and generic network access device 15 can be facilitated in the manner discussed in connection with FIGS. 2 and 3, and elsewhere herein. For example, the processor 402 of the PIMD 13 can execute program instructions stored in memory 401 to cause the PIMD 13 to wirelessly send data to, and receive data from, the IFD 14 using the communications circuitry 409 of the PIMD 409 and the communications circuitry 410 of the IFD 14. The data may be transferred between the PIMD 13 and the IFD 14 using inductance and/or RF based communication (e.g., Bluetooth or other PAN protocol), among other methods. In this way, an IFD 14 can function as an information buffer for transfer of the data across a network using one or more generic network access devices 15 to an APM server 490 or other destination.

Multiple types of generic network access devices 15 are represented in FIG. 4, including a cellular telephone, laptop computer, PDA, wireless router, and LAN. However, one having ordinary skill in the art will realize upon reviewing this disclosure the great variety of types of generic network access devices that can be used in accordance with the present invention as a generic network access device 15 in accordance with the present invention. The multiple types of generic network access devices are illustrated in FIG. 4 and discussed herein to demonstrate that an IFD can use a variety of different types of generic network access devices to facilitate data transfer between a PIMD and a remote server. In this way, an IFD provides flexibility in allowing a patient to use any number of generic network access device that can be easily obtained by a patient at a general electronics store to provide connectivity between a PIMD and a remote server via a public communication infrastructure that comply with regulatory standards for medical information transmission, while minimizing the use of specially designed, certified, and manufactured medical information transmission equipment.

To facilitate use of a variety of different generic network access devices 15, IFD 14 includes a protocol library 420 which stores a variety of access protocols in memory. Therefore, the IFD 14 can use a communication protocol from the protocol library 420 matched for the particular type of generic network access device 15 and protocol 470 associated with the generic network access device 15, and switch communication protocols when necessary and/or advantageous.

For example, a patient with a PIMD 13 may be using a first cell phone functioning as a generic network access device 15 to facilitate data transfer between the PIMD 13 and the APM server 490, the first cell phone using GSM. To facilitate data transfer, the IFD 14 contains program instructions stored in the protocol library 420, executable by the processor 425, to condition the data received by the PIMD 13 (e.g., transferred via Bluetooth protocol) for transmission across a GSM network. In this way, the IFD 14 is configured to facilitate translation of data for transmission between different networks and channels that use different transfer protocols, hardware, software, firmware, and the like.

Continuing with the example, the patient may then lose the first cell phone or travel to a location that does not provide cellular support for the first cell phone. The patient may then acquire a different generic network access device 15, such as a second cell phone configured to operate only on a UMTS network. The protocol library 420 of the IFD 14 allows the IFD 14 to utilize a variety of different generic network access devices 15, as information regarding the conditioning of data for transmission on a variety of disparate networks using disparate protocols is stored in the protocol library 420. As used herein, conditioning of information refers to a process of handling the information that can include translation of the data between disparate communication protocols and formatting the data in compliance with medical regulatory standards for transmission across generic public networks.

An IFD 14 of the present invention allows a patient to use a variety of different generic network access devices 15, and not be constrained by a single dedicated device that is specially configured and certified to access a network and handle medical information. The worldwide commercial availability of generic network access devices means that a patient's PIMD 13 can send information to, and receive information from, an APM server 490 or the like, despite loss of equipment or travel through different network coverage areas. Additionally, the IFD 14 allows practically any generic network access device to be used to facilitate data transfer, such that the generic network access device is not specially configured to, and/or certified by a regulatory agency to, properly handle medical information and interface with the PIMD (i.e., the network access device can be generic). In this way, a patient can purchase or otherwise acquire practically any off-the-shelf cellular telephone or similar generic network access device to facilitate data transmission. This minimizes the equipment that must be specially manufactured and purchased and maximizes the convenience for the patient while maintaining compliance with medical data transmission standards.

Partitioning 440 by the IFD 14 can facilitate compliance with standards for medical data transmission even though generic network access devices 15 are used. As illustrated in FIG. 4, the IFD 14 is shown to have created a partition 440 for handling medical information, whereby devices on the private side 450 of the partition are specifically configured to properly handle medical information (e.g., Class III medical devices) while devices on the public side 460 of the partition need not be specifically configured to handle medical information.

Before data is sent from a Class III medical device to a device agnostic with respect to medical data regulation (such as the hardware and protocols of the devices of 470), the data can be conditioned for transmission across networks of the public side 460 of the partition 440. Such conditioning can format the information, where such formatting can include, but is not limited to, encrypting, de-identifying (stripping of patient identifying information), and adding validation keys (to insure integrity of data by recipient).

Conditioning can include establishing a virtual private network between a remote server and a patient implantable medical device and/or IFD. In some embodiments, the establishment of a virtual private network can be facilitated by secure sockets layer, whereby an implanted medical device and/or IFD presents a remote server with a list of supported ciphers and hash functions and the remote server selects from these on the basis of strength. A digital certificate can then be sent to the patient implantable medical device and/or IFD with an encryption key. A virtual private network can facilitate sender authentication and message integrity.

To the extent that IFD 14 conditions the medical data for handling by generic network access devices 15 and transmission across public networks with various devices and protocols 470, private server 445 may process the data to de-encrypt, re-identify, and/or validate keys, such that private server 445, computer 495, APM server 490, and components of the private network 480 are specially configured to be compliant medical devices (e.g., certified Class III medical devices) that follow appropriate procedures.

In some embodiments, at least some of a plurality of generic network access devices (e.g., 15) comprise one of a plurality of different cellular telephones each using a different one of the plurality of disparate communication protocols (e.g., 470), and an interface device (e.g., 14) is configured to facilitate transmission of PIMD data in compliance with a predetermined medical device regulatory requirements specification (e.g., as stored in 430) between a PIMD (e.g., 13) and a remote server (e.g., 490) via a public network (e.g., 375) using any one of the plurality of different cellular telephones without being reconfigured to facilitate transmission of PIMD data in compliance with the predetermined medical device regulatory requirements specification when switching use of different ones of the plurality of different cellular telephones.

As shown in FIG. 4, and shown and described elsewhere herein, a method, implemented by use of an interface module (e.g., 14) transportable by an ambulatory patient, can be implemented for facilitating transfer of medical information between a PIMD (e.g., 13) and a remote network server (e.g., 490). The method can include communicating medical information between the PIMD and the interface module via a first channel (e.g., using 409 and 401) and in compliance with a predetermined medical information regulatory standard (e.g., using 430), preventing access to the PIMD via the interface module other than through the first channel, detecting a communication protocol used by an available generic network access device (e.g., 15), selecting a communication protocol rule set from a plurality of communication protocol rule sets (e.g., using 420) to effect communication between the interface device and an available generic network access device of a plurality of generic network access devices, each of the protocol rule sets associated with one of the disparate communication protocols, and transferring at least some of the medical information to a remote network (e.g., 480) via a second channel established between the interface module and the available generic network access device using the selected communication protocol rule set, wherein the at least some of the medical information is transferred between the interface device and the remote network in compliance with the predetermined medical information regulatory standard. In such an embodiment, communicating and transferring at least some of the medical information in compliance with the predetermined medical information regulatory standard may comprise encrypting, de-identifying, and adding authentication elements to the at least some medical information. Such an embodiment may further include de-encrypting, re-identify, and authenticating the medical information using a server (e.g., 409) of the remote network after the at least some medical information has been transferred to the remote network. Such a method may further include remotely reprogramming the PIMD from the remote network using the first channel and the second channel. Such a method may further include detecting an additional communication protocol used by an additional generic network access device of the plurality of generic network access devices, selecting an additional communication protocol rule set from the plurality of communication protocol rule sets to effect communication between the interface device and the additional generic network access device, and transferring at least some of the medical information to the remote network via a third channel established between the interface module and the additional generic network device using the selected additional communication protocol rule set, wherein the at least some of the medical information is transferred between the interface device and the remote network in compliance with the predetermined medical information regulatory standard.

Figure 5:
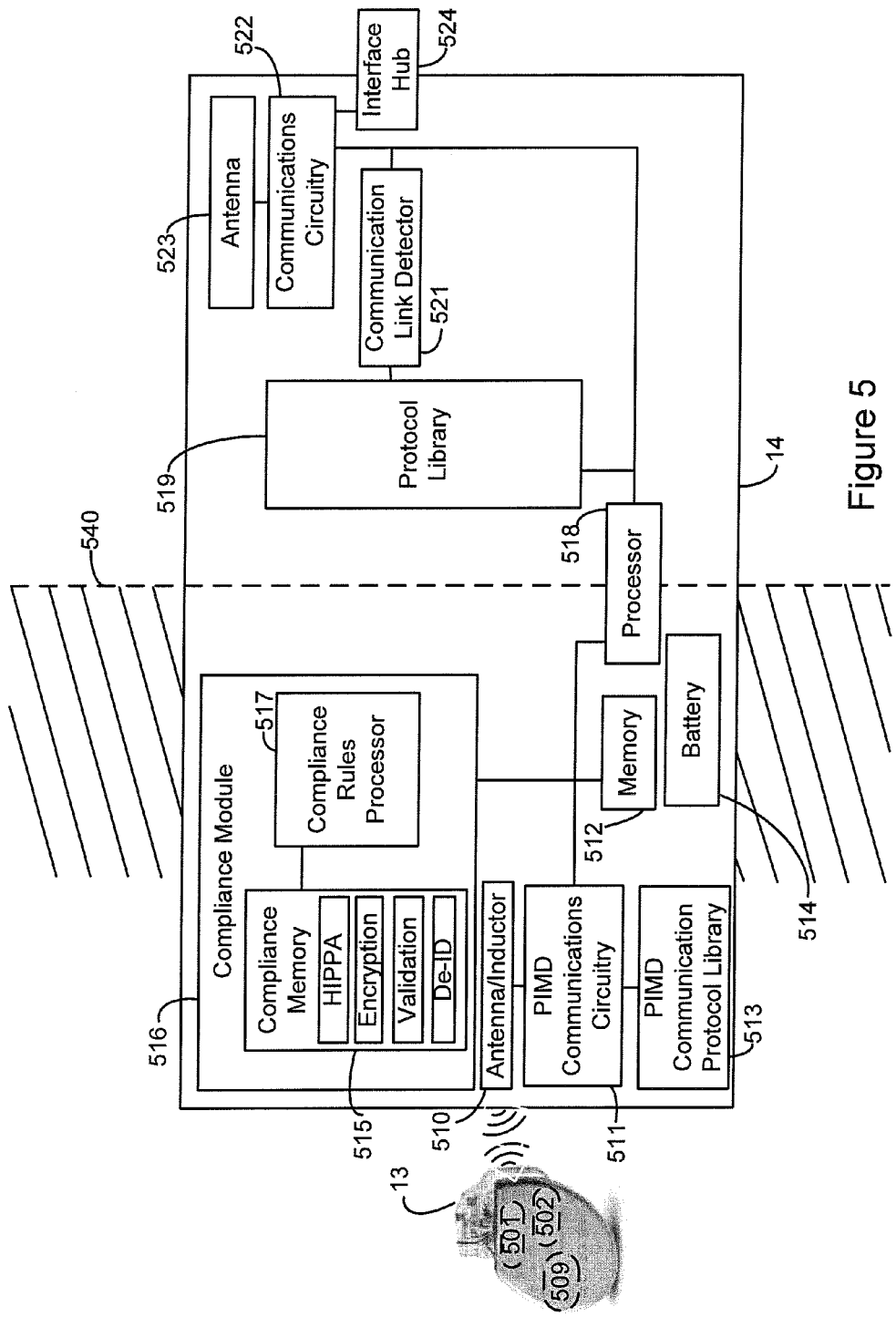
FIG. 5 shows block circuitry diagrams of a patient implantable medical device and an interface device in accordance with various embodiments of the present invention.

FIG. 5 illustrates some components of an IFD 14 and a PIMD 13, which can be the same IFD 14 and PIMD 13 discussed and represented elsewhere herein, such as in FIGS. 1, 2, 3, and 4, for example. PIMD 13 includes memory 501 containing program instructions executable by a processor 502 to cause communication circuitry 509 to send information to, and receive information from, the IFD 14. The IFD 14 includes program instructions stored on memory 512 and executable by the processor 518 to cause the PIMD communications circuitry 511 to send information to, and receive information from, the PIMD 13 via antenna/inductor 510.

To aid in communication between PIMD 13 and the IFD 14, the IFD 14 includes PIMD communication protocol library 513, which contains information that can facilitate the transfer of information between the IFD 14 and a variety of different PIMD's using disparate communications methods and protocols. For example, PIMD 13 and IFD 14 may communicate using RF and/or inductance methods, and may further use MICS, Zigbee, Bluetooth, and/or UWB protocols, among others. Likewise, the IFD 14 can communicate with a variety of others devices, including PIMD's, using the PIMD communication protocol library 513, PIMD communications circuitry 511, and antenna/inductor 510.

Information collected from the PIMD 13 or other device can be translated and conditioned by the compliance module 516 before being passed wholly across partition 540. Conditioning of medical data can be a prerequisite for transmission of the data past the partition 540 to carry out the methods discussed herein to comply with medical information handling standards.

Compliance module 516 can contain program instructions stored in compliance memory 515 executable by the compliance rules processor 517 to carry out various medical data conditioning functions. For example, compliance module can be configured to format data by encryption, implementation of data integrity validation, de-identification of the data, and/or implementation of HIPPA compliance functions, among others. The formatted medical data can be passed across the partition 540, and may be further conditioned, such as undergoing translation between communication protocols.

As such, compliance module 516 can facilitate processing of PIMD data in accordance with compliance rules to encrypt, de-identify, and adding authentication elements to the PIMD data, among other functions, consistent with a predetermined medical device regulatory requirements specification.

The medical data can be translated to account for disparate communication protocols to facilitate transmission. In some cases, medical data will need to be translated because it was received by the IFD 14 using one communication protocol (e.g., Bluetooth) and needs to be transmitted using a different protocol (e.g., GSM). Translation instructions stored in protocol library 519 can be executed by processor 518 to translate the data as needed to match disparate incoming and outgoing communication protocols.

Medical information can be sent to, and received from, a generic network access device using the communications circuitry 522, antenna 523, and interface hub 524. For example, interface hub 524 can include a USB or Firewire plug-in to connect with a generic network access device that is likewise enabled. Alternatively, or additionally, signals may be sent and received via antenna 523 to communicate with communications circuitry and an antenna of a generic network access device using various protocols, including but not limited to Bluetooth and/or 802.11, among others.

Communication link detector 521 can be used to detect when a generic network access device is accessible and to further characterize a detected generic network access device, such as by use of any known network discovery software. Communication link detector 521 can use communications circuitry 522, antenna 523, and/or interface hub 524 to detect and characterize a generic network access device. For example, communication link detector 521 can monitor and/or ping the channels available via the communications circuitry 522, antenna 523, and interface hub 524.

Once a generic network access device is detected, it can be characterized. Characterization can include sending messages (e.g., predetermined queries) to a generic network access device using various communications protocols across various channels to elicit response from various services. The response of the generic network access device can indicate which protocols and functions are available on the detected generic network access device. For example, if the generic network access device responds to a specific command sent using GSM protocol with a predetermined answer using GSM protocol, then it can be concluded that the generic network access device is enabled for GSM based communication. In embodiments where the generic network access device is a cellular telephone, then an exemplar command that could be sent to the cell phone could include request that the cell phone register with a cell tower and/or request a power level response from the cell tower.

The characterization of a generic network access device by an IFD can help determine the manner in which the IFD conditions medical information. A characterization indicating which protocol(s) are enabled on a generic network access device compared to the protocol used to communicate between a PIMD and the IFD can determine the translation between protocols that needs to take place between incoming and outgoing data transmissions.

Characterization to detect a communication protocol used by an available generic network access device (e.g., 15) can include sending a plurality of stored inquiry commands to the available generic network access device and monitoring for one or more predetermined responses from the available generic network access device, the one or more predetermined responses indicating what functions are enabled on the available generic network access device. In such a way, an interface device (e.g., 14) can include program instructions stored in protocol memory (e.g., 519) and executable by a processor (e.g., 518) to cause the interface device to send a plurality of stored inquiry commands to an available generic network access device (e.g., 15) using the second communications interface (e.g., 521, 524, 522, 523) and monitor for one or more predetermined responses from the generic network access device, the one or more predetermined responses indicating functions that are enabled on the communications device.

As shown in FIG. 5, and shown and described elsewhere herein, some embodiments of the invention can include an interface module (e.g., 14) for facilitating communication and data transmission between a PIMD (e.g., 13) and a remote server (e.g., 490). Such an interface module can include first circuitry comprising a first communications interface (e.g., 510, 511, 513) configured for communication with a PIMD and a regulatory compliance module (e.g., 516) having an input coupled to the first communications interface, an output, and a regulatory memory (e.g., 515) for storing compliance rules consistent with a predetermined medical device regulatory requirements specification, the compliance module configured to moderate communicative interaction between the PIMD and the first circuitry and to process PIMD data in accordance with the compliance rules. The interface module can further include second circuitry having an input coupled to the output of the compliance module comprising a protocol library (e.g., 519) comprising sets of communication protocol rules, each communication protocol rule set associated with one of a plurality of disparate communication protocols and a second communications interface (e.g., 522, 523, 524) coupled to the protocol library and configurable to implement any one of the communication protocol rule sets, the first communications circuitry partitioned from the second communications circuitry such that the PIMD data is communicated to the input of the second circuitry only via the output of the compliance module. The interface module can further include a processor (e.g., 518) coupled to the first and second circuitry, the processor configured to detect a communication protocol used by an available generic network access device of a plurality of generic network access devices (e.g., 15) and select a communication protocol rule set from the protocol library for implementation by the second communications interface to effect communication between the interface module and the available generic network access device. The interface module can further include a housing configured to house the first communication circuitry, the second communication circuitry, and the processor.

As discussed herein, a PIMD may be remotely programmed by a remote server (e.g., 490) using an interface module (e.g., 14). For example, the interface module may be configured to facilitate remote access to the PIMD via a communications interface (e.g., 510, 511), a second communications interface (e.g., 522, 523, 524), and a generic network access device (e.g., 15), and a regulatory compliance module (e.g., 516) is further configured to limit non-authenticated remote access to the PIMD.

Figure 6:
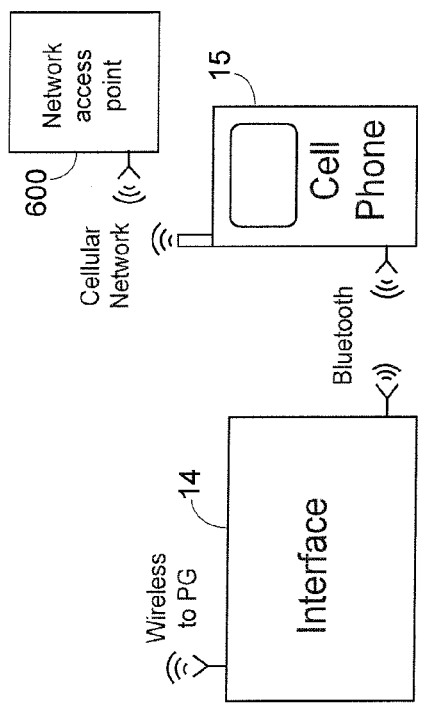
FIG. 6 shows block diagrams of an interface device and a generic network access device in accordance with various embodiments of the present invention.
Figure 7:
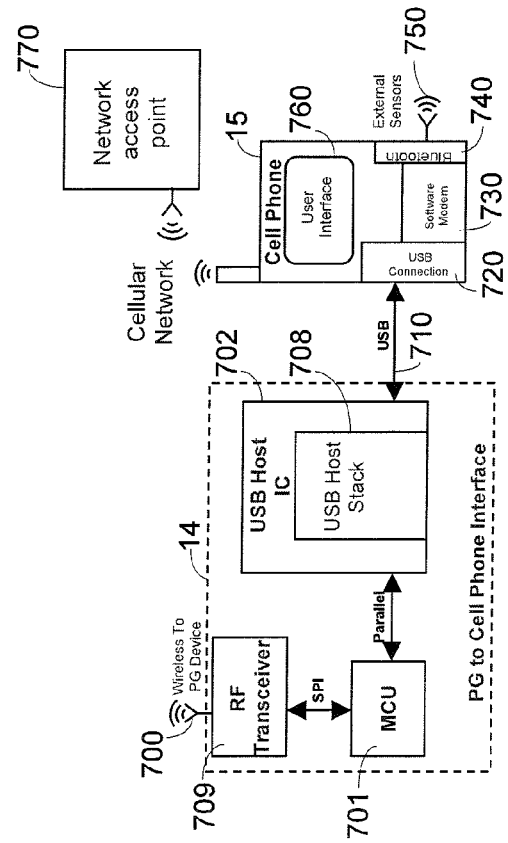
FIG. 7 shows block circuitry diagrams of an interface device and a generic network access device in accordance with various embodiments of the present invention.

FIGS. 6 and 7 illustrate various aspects of the present invention. The embodiments of FIGS. 6 and 7 could be the same embodiments illustrated in FIGS. 1, 2, 3, 4, and/or 5, with various aspects emphasized and deemphasized.

FIG. 6 illustrates data transfer between a wireless PG device (not illustrated) and an APM server (not illustrated) using an IFD 14, a generic network access device 15 (labeled as a cellular telephone), and a network access point 700 as intermediaries.

FIG. 7 illustrates an IFD 14 connecting to generic network access device 15 (labeled as a cellular telephone) via USB connection. A USB connection between the IFD 14 and generic network access device 15 can be used to transfer information between a programmable (PG) device (not illustrated) and a network access point 770 using antenna 700, and RF transceiver 709. Data is passed through the MCU 701 and USB host IC of the IFD 14, which may further condition the data, as discussed herein.

The USB connection is facilitated by USB host integrated circuit (IC) 702, USB host stack 708 containing protocol for connecting with a variety of different generic network access devices via USB connection, USB cord 710, and USB connection 720 of the generic network access device 15. As illustrated in FIG. 6, connections facilitating data transfer via an IFD 14 and generic network access device 15 can include USB, parallel, serial peripheral interface, and/or universal asynchronous receiver/transmitter connections, among others.

USB host IC 702 may be used in requisition of functions of the generic network access device 15 for data transfer, gathering patient information, and communicating with external sensors 650 (e.g., scale and/or blood pressure device). For example, USB host IC 702 may push a protocol stack to a generic network access device 15. Execution of the stack can allow control of low level functions of the generic network access device 15 by the IFD 14, including use of Bluetooth module 740 for communication with external sensors and/or using the interface 760 to present information to a patient and gather information from the patient (e.g., queries concerning patient status and symptoms). The software modem 730 allows software, and not specific hardware, to operate modem functions, thereby providing enhanced flexibility.

Figure 8:
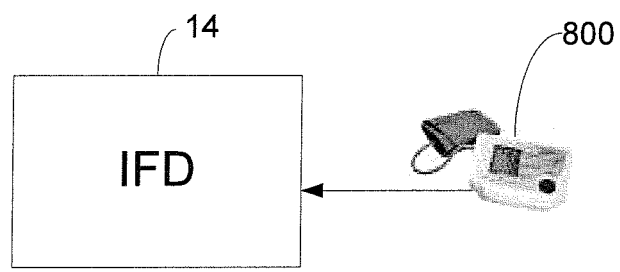
FIG. 8 is a block diagram showing a medical device interacting with an interface device in accordance with various embodiments of the present invention.

FIG. 8 illustrates a blood pressure device 800 configured to transmit information to an IFD 14 via a direct connection. Although a blood pressure device 800 is illustrated in FIG. 8, many other implantable and external sensor based devices could be used as described herein for collecting and transferring data. The blood pressure device 800 can be enabled with communications circuitry and protocol for transmission of collected blood pressure data to the IFD 14. For example, the blood pressure device 800 could transmit data to the IFD 14 using a wired connection, including but not limited to USB, Firewire, and/or other protocol, or a wireless connection, including but not limited to Bluetooth, IEEE 802.15, ZigBee, and/or other protocol.

Figure 9:
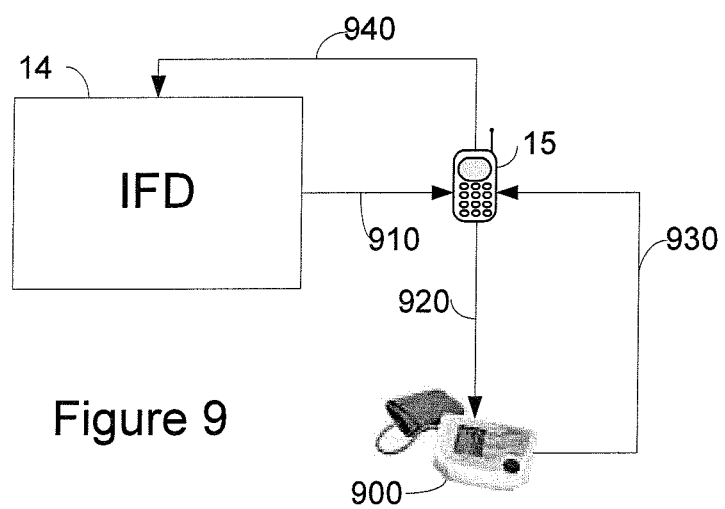
FIG. 9 is a block diagram showing a medical device interacting with an interface device using a generic network access device in accordance with various embodiments of the present invention.

FIG. 9 illustrates a blood pressure device 900 configured to transmit information to an IFD 14 via a generic network access device 15. A direct connection may not be possible or convenient between some IFD's and sensors. In such embodiments, IFD 14 may be used to requisition low level functions of the generic network access device 15 to facilitate connection with blood pressure device 900, as discussed herein. The IFD 14 and the generic network access device 15 may be connected using any means discussed herein, such as USB. After pushing a protocol stack to the generic network access device 15, the IFD 14 may send an SMS message to generic network access device 15 requesting that the generic network access device 15 perform a search of available sensors, such as for the blood pressure device 900.

To collect data, IFD 14 can send 910 a SMS message to generic network interface device 15 requesting data of one or more sensors. How the generic network access device 15 communicates with the blood pressure device 900 depends on what functions on the generic network access device 15 have been requisitioned by the IFD 14 and what communication protocols are common between the generic network access device 15 and the blood pressure device 900. For example, lower band frequencies and/or Bluetooth communication functions may have been requisitioned that match the communication capabilities of the blood pressure device 900. If Bluetooth functionality of the generic network access device 15 has been requisitioned and matches the communication functionality of the blood pressure device 900, then the generic network access device 15 can then send 920 a message to blood pressure device 900 requesting data. Blood pressure device 900 can then send 930 the data to the generic network access device 15, which can translate the data to be sent 940 via USB to the IFD 14.

Figure 10:
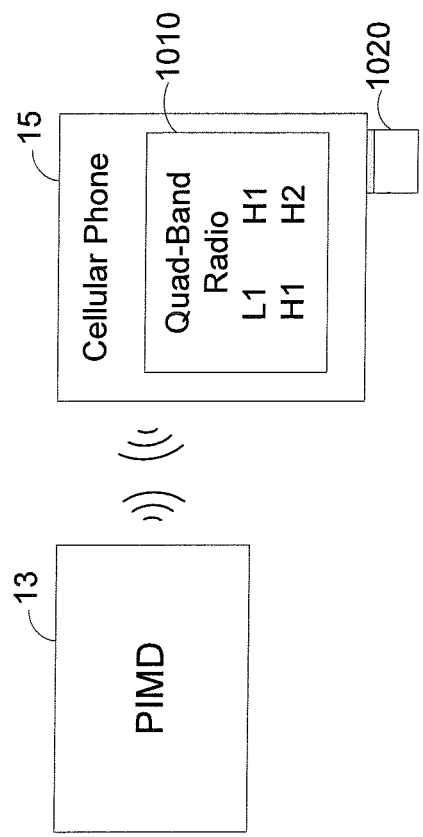
FIG. 10 is a block diagram showing a patient implantable medical device interacting with a generic network access device in accordance with various embodiments of the present invention.

FIG. 10 illustrates a PIMD 13 and a generic network access device 15, which can correspond to the embodiments discussed herein. Generic network access device 15 includes quad-band radio 1010 having lower bands L1 and L2 and higher bands H1 and H2. These bands can be used to communicate with a mobile network, such as directly with a network tower.

In the embodiment of FIG. 10, an IFD 1020 has been plugged into the generic network access device 15. The IFD 1020 can contain the circuitry configured for conditioning medical data and commands as discussed herein, such as a compliance module. As discussed herein, an IFD can requisition functions of a generic network access device, such as a cellular telephone. Such functions can include control over one or both lower level radio bands (L1 and L2) of the quad-band radio 1010. The IFD 1020 can then use a requisitioned lower level radio band for communicating with PIMD 13 using the quad-band radio 1010. To accomplish this, the IFD 1020 can supply the appropriate communication protocol and/or processing to conduct communication with the PIMD 13 using the quad-band radio 1010.

Even through the IFD 1020 has requisitioned some functionality of the generic network access device 15, the intrusion should be minimal and allow the generic network access device 15 to substantially operate as originally configured (e.g., in accordance with a "factory" or "default" configuration). In this way, a partition has been created with respect to the operation of the generic network access device 15, allowing normal non-medical use (e.g., voice and data transmissions by the user) of the device and use of the device compliant with regulatory standards for transmission of medical information subject to on-board resource (e.g., antenna, band) availability.

Figure 11:
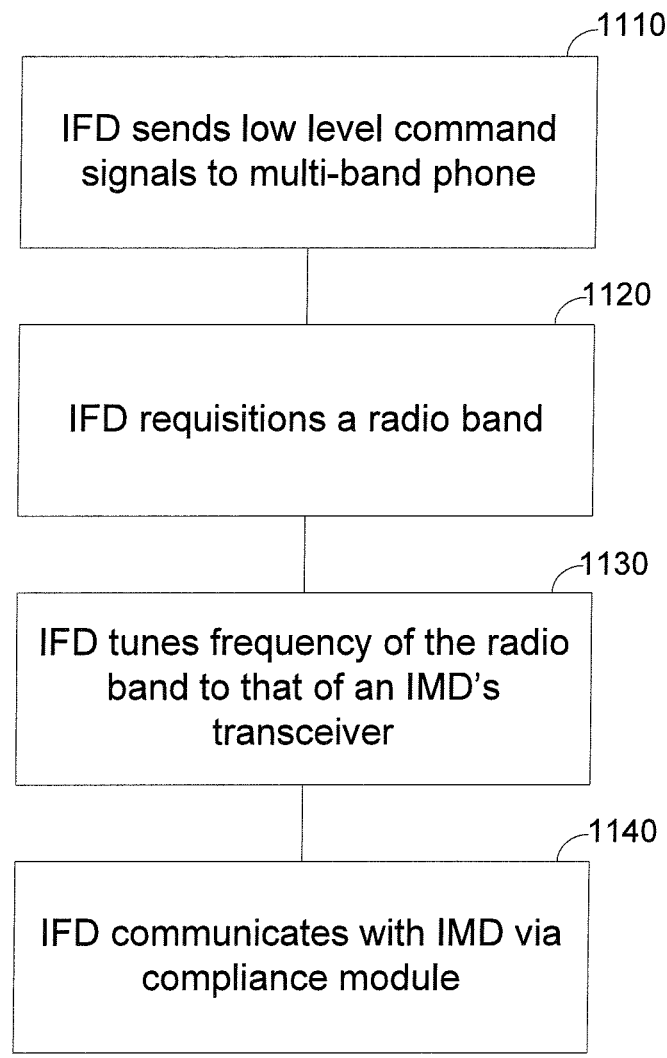
FIG. 11 is a flow diagram showing a method for the requisition of functions of a generic network access device by an interface device in accordance with various embodiments of the present invention.

FIG. 11 demonstrates a method for requisition of communication functionality. The method of FIG. 11 can be performed using the embodiments discussed and illustrated herein. The method of FIG. 11 includes an IFD sensing 1110 low level command signals to a multi-band phone. These low level command signals may be used by the IFD to requisition 1120 a radio band of the multi-band phone. The IFD can then tune 1130 the frequency of the requisitioned band to the frequency of a PIMD's transceiver. The IFD can then communicate 1140 with the PIMD via the requisitioned radio band using the compliance module to condition and translate medical data and commands, as discussed herein.

In such a way, data link layer commands can be sent to a generic network access device from an interface module to control a subset of function of the generic network access device. Furthermore, control of the functions can facilitate transferring information between the a generic network access device and a sensor-based patient data collection device, wherein the data link layer commands are used to requisition control of the subset of functions of the generic network access device to facilitate communication with the sensor-based patient data collection device.

Figure 12:
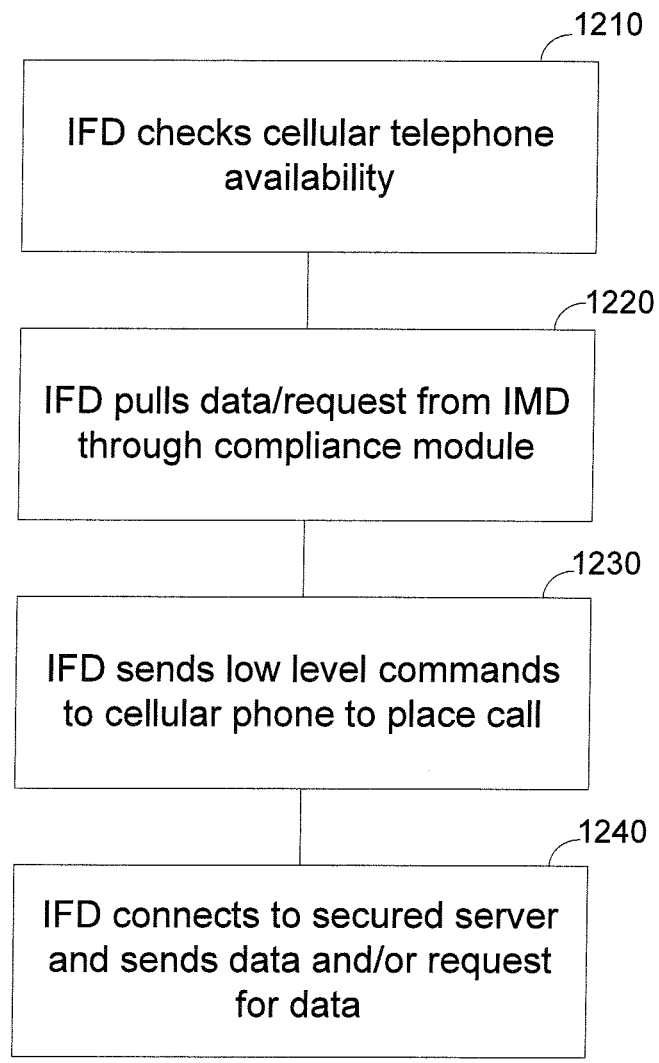
FIG. 12 is a flow diagram showing a method for facilitating connectivity between a patient implantable medical device to a secured server using an interface device in accordance with various embodiments of the present invention.

FIG. 12 demonstrates a method of the present invention for connecting to a network. The method of FIG. 12 can be implemented by the embodiments discussed herein. The method of FIG. 12 includes an IFD checking cellular telephone availability. The cellular telephone can be a generic network access device as discussed herein, and the IFD and the cellular telephone can communicate using the means discussed herein. When it is determined that a cellular telephone is available, the IFD can pull 1220 data and/or requests from the PIMD through a compliance module of the IFD.

IFD can then send 1230 low level commands to the cellular telephone to place a call using voice or data functionality, depending on what is available. IFD can then connect 1240 to a secured server and send data and/or requests for data.

It is noted that steps 1210, 1220, and 1230 can be performed in an order different from that presented, including simultaneously. However, it may be advantageous to first determine the availability of a cellular telephone, and the available functionality of the cellular telephone, before pulling, and conditioning data to best match available protocols in an efficient matter.

As described above, commands may be sent from the APM 16A to the IFD 14 using messaging services supported by the mobile network 20 infrastructure illustrated in FIG. 2. One embodiment of the invention involves using Short Message Service (SMS) or "text messages" to direct commands to the IFD 14 for ultimate delivery to the PIMD 13. Verification techniques may be employed to ensure that an SMS message from an unauthorized source is not inadvertently addressed to the IFD 14 and perceived as a command. In one embodiment, a subset of the data in the SMS message may be used by the IFD 14 to verify that the SMS message originated from an authorized source (e.g., APM 16A). One example involves the IFD 14 comparing the source address (e.g., MSISDN number) of the SMS message with a stored list of approved source addresses. In another exemplary embodiment a code may be inserted into the SMS message itself. For example, a standard SMS message supports 160 characters, and the first predetermined number of characters may represent a code used by the IFD 14 to verify that the sender is genuine. The code may be the concatenated PIMD/PC identifiers signed with the APM server's private key. The APM server's private key can be verified by both the PC and the PIMD as they have the public key for the server in their set of certificates. Message verification techniques utilizing handshaking may also be used.

Figure 13:
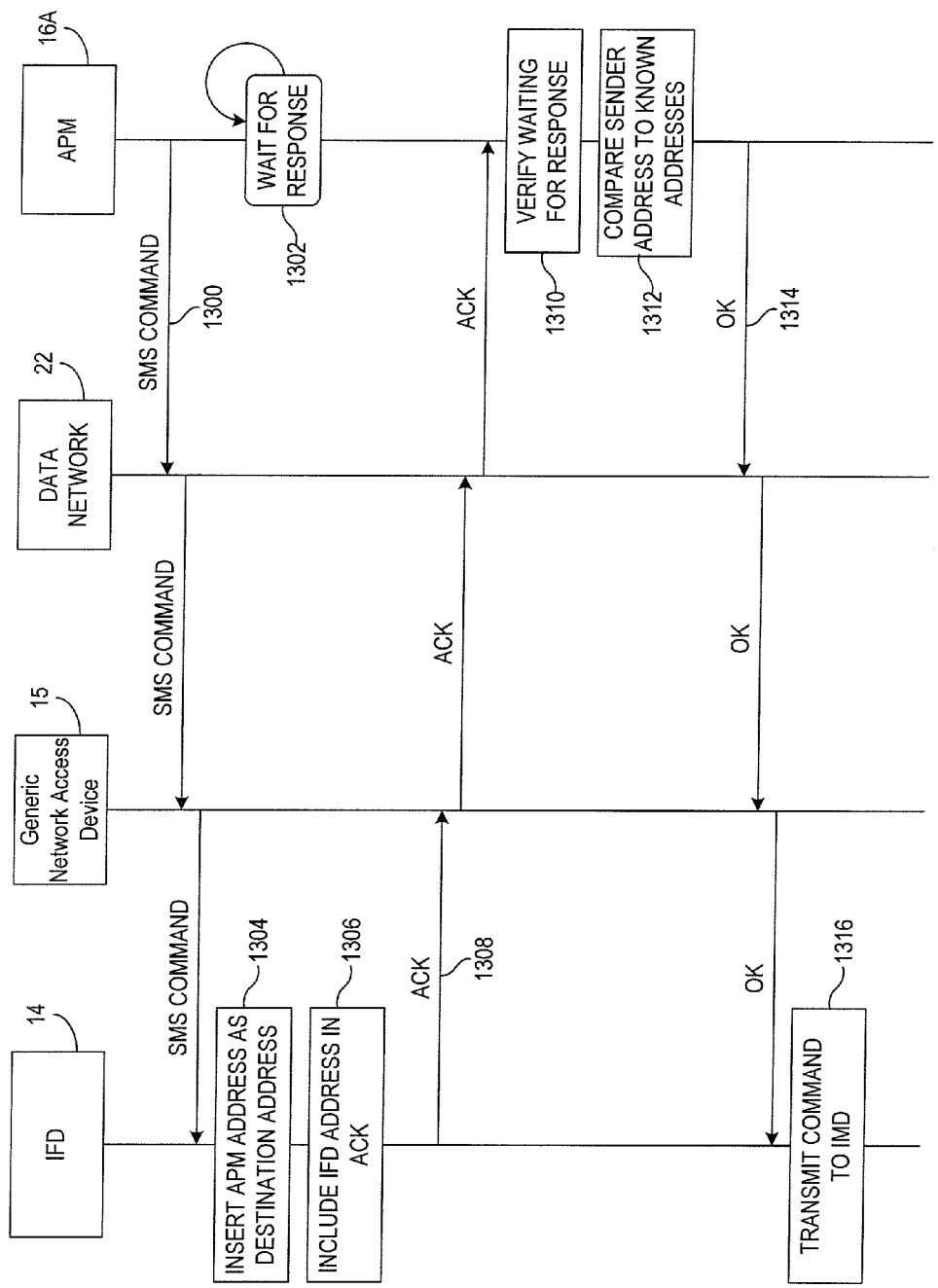
FIG. 13 is a diagram showing a method for facilitating connectivity between a patient implantable medical device to a secured server of an advanced patient management system using an interface device and a generic network access device in accordance with various embodiments of the present invention.

FIG. 13 is a message flow diagram illustrating one manner of using acknowledgment messages to verify the source of the SMS (or other) message. Such a handshaking embodiment enables the IFD 14 to verify that the command originated at an APM 16A or other authorized source before forwarding the command to the PIMD 13. This may be beneficial, for example, where the IFD 14 is unaware of the APM 16A source address. The IFD 14 may be generally unaware of APM addresses, or new APMs having new source addresses may be added to the system unbeknownst to the IFD 14.

Operationally, the APM 16A may direct a command to the IFD 14 via an SMS-based command 1300. If the APM 16A was in fact the source of the SMS message, it enters a wait state 1302 or otherwise notes that it has initiated the message. The command is forwarded through the data and mobile networks 22, 20, and arrives at the IFD 14. Rather than "reply" to the source address of the incoming SMS message, the IFD 14 inserts 1304 a known APM address as the destination address. Thus, even if the SMS message originated at an unauthorized source, the resulting acknowledge message (ACK) 1308 is directed to the APM 16A. Additionally, the sender's address (i.e., the source address identified in the received SMS message) can be included 1306 in the responsive ACK message, for reasons discussed more fully below.

When the ACK 1308 arrives at the APM 16A, it verifies 1310 that it was in a wait state, waiting to receive an ACK message from the IFD 14. If it was not, it can be assumed that the SMS message received at the IFD 14 was not issued by the APM 16A, and the APM 16A can notify the IFD 14 as such. Further, the sender address provided by the IFD 14 in the ACK message can be compared 1312 to a set of known APM addresses, if multiple APM and corresponding APM addresses exist. If the received sender address does not correspond to any known APM addresses, it again can be assumed that the original SMS message received at the IFD 14 was not initiated by the APM system. If the received sender address matches a known APM address, the APM sends an OK 1314 or other confirmatory message to notify the IFD 14 that the original SMS message was indeed issued by the APM system. Upon receipt of the OK 1314 message, the IFD 14 can transmit 1316 the command embodied within the SMS message to the PIMD 13 or other medical device paired with the IFD 14. Additional or alternative processes for message verification that may be used are described in commonly owned U.S. Patent Publication No. 2007/0185547, which is incorporated by reference herein.

The invention may incorporate various methodologies for providing secure and reliable communication, including features described in one or more of the following references: U.S. Patent Application Publication Nos. 2007/0053516, 2007/0049992, 2007/0100396, 2007/0049983, 2007/0195163, 2007/0106433, 2007/0118188, 2007/0083246, and U.S. Pat. Nos. 7,218,969, 7,203,545 all of which are incorporated herein by reference.

An IFD in accordance with embodiments of the present invention may be dynamically configurable via interaction with an APM server and/or a PIMD. This capability of dynamically altering the configuration of the IFD serves to enhance cooperative operation between the IFD, PIMD, and APM system.

IFD firmware may be updated by server push to the IFD through a connected generic network access device. In some configurations, two flash memories are provided in the IFD for storing firmware, where one flash memory set is used to store a current configuration and the second is overwritten during an updating procedure. Updating in this manner serves as a failsafe, as one complete set of operating instructions are preserved in case the update is unsuccessful.

As discussed herein, PIMD can be remotely reprogrammed by a health care professional. Access control to a PIMD can be in important feature for protecting the integrity of the PIMD and complying with regulatory standards. Access control can be accomplished through authentication, which refers to procedures established to verify that the device requesting access to a PIMD via an IFD is the device that it purports to be. For example, a unique identifier(s) from a PIMD may be used as a key to authenticate the device. A more secure process involves specific keys and certificates programmed into the PIMD that allow the PIMD to authenticate messages from the server. The PIMD may use its ability to authenticate the server as a way to authenticate the IFD. A useful authentication method is the "challenge/response" approach described below.

It is preferable, but not necessarily required, that an IFD be uniquely assigned to a patient, such as through a process generally referred to herein as "pairing." As used herein, pairing generally refers to the unique association created between a patient's IFD 14 and the medical device(s) associated with that patient, such as a PIMD.

Authentication can be further bolstered in various ways, including encrypting the identifier, or subjecting the identifier to a cryptographic hash function. A cryptographic hash function generally uses a character string or message of any length as input, and in response generates a fixed-length string output often referred to as a digital fingerprint. The unique identifier of the PIMD could be used as the input. Alternatively, the PIMD identifier can be concatenated with a unique identifier of the IFD, such as the Mobile Station Integrated Services Digital Network (MSISDN) number (i.e., the "phone number" or other address of a generic network access device) for use with authentication processes. A cryptographic hash function may optionally be applied to the conjoined result and used for access control. These and/or other security measures are employed in various embodiments of the invention.

Authorization processes may also be used at the IFD and/or APM. Authorization in this sense generally refers to functionality at the relevant device or system that protects the device from communicating unless it is granted authority to do so. Authentication and/or authorization may use unique identifiers or certificates and cryptographic keys to determine whether device functionality (authorization) or network access (authentication) is allowed. For example, in one embodiment, the unique identifier(s) from the PIMD may be used as a key to authorize communication functionality on the IFD.

An IFD can provide virtual connections routed through public networks to separate the traffic of the intended and unintended communication nodes over the underlying networks. Firewalls may also be used, which provides a barrier on the IFD or other bottleneck channel. These firewalls can restrict the number of open ports, specify what type of packets are passed through, and specify which protocols can pass. Information communicated via these restricted channels can further be encrypted, which involves encoding the data into a form that only the other intended elements can decode. Because the IFD is exposed on the cellular network, a firewall is used to prevent unauthorized access attempts.

Remote programming of a PIMD may be initiated by caregiver action and may end with the reporting of the success or failure of the application of the programming to the intended PIMD back to the caregiver. Remote programming is performed as a sequence of operations, which, in specific instances, can be suspended or broken at specific points as necessary.

Initially, a caregiver performs a remote programming session through a data entry mechanism (such as computer 495 of FIG. 4). Caregiver-selected programming instructions and parameters are translated by a regulated server into PIMD-formatted commands, which are checked for correctness and digitally signed. The PIMD-formatted commands are also reverse translated and provided to the caregiver in displayable form for acceptance or rejection. If the translated programming is rejected by the caregiver, control reverts back to the caregiver programming session. Otherwise, the PIMD-formatted commands are marked for delivery to the server 390 and, following receipt by the server, are verified for authenticity and integrity. In a further embodiment, the PIMD 13 itself also performs verification of the commands, either in addition to or in lieu of the server. The server 390 performs a programming session. If the session is interrupted and not resumed, or abnormally terminates, the original PIMD 13 programming is restored and control reverts back to the programming session. Upon successful programming, the server interrogates the PIMD 13 following programming session completion to report post-programming results to the caregiver for review and evaluation. Additional implementations for remote programming, aspects of which may be used in conjunction with various embodiments discussed herein, are described in commonly owned U.S. Patent Application Publication Nos. 2007/0185547 and 2007/0195163, which are incorporated herein by reference.

In some embodiments of the present invention, an IFD can monitor for the presence of a generic network access device to facilitate data transmission, and alert a patient when no generic network access device is available to facilitate data transmission. Such an alert could indicate to the patient that a previously used generic network access device is missing, malfunctioning, missing a component or resource (e.g., battery power) out of range of the IFD, and/or out of service range (e.g., cellular service range). Such an alter could indicate to the patient that the generic network access device needs attention (e.g., battery charging or replacement), that that patient needs to seek service coverage, and/or needs to acquire a different generic network access device (e.g., a cellular telephone with better service coverage for the current area). Such an indication could be displayed on an interface of the IFD, on an interface of the generic network access device, via text or voice message, email, and/or some other vibratory alert, visual alert, and/or audible alert.

The IFD may include a proximity detector that determines if a generic network access device is sufficiently close to the IFD to maintain communication between the devices. Alternatively or additionally, the IFD may include a proximity detector that determines if a PIMD is sufficiently close to the IFD to maintain communication between the devices. One or more of the above described alerts could be issued if a proximity detector indicates that devices are out of communication range.

In another example, if the PIMD has not communicated with the IFD for a predetermined time interval, the PIMD and/or the IFD may notify the patient, such as by vibratory alert. In another example, if the IFD has not communicated with a generic network access device and/or detected the presence of the same for a predetermined time interval, the generic network access device and/or the IFD may notify the patient, such as by text or voice message.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

We claim:

1. An interface device for facilitating transfer of medical information between a patient implantable medical device (PIMD) and a remote network server via public network infrastructure using any of a plurality of generic network access devices having disparate communication protocols, the interface device comprising:
   a housing configured for portability by an ambulatory patient;
   first communication circuitry provided in the housing and configured to effect communication between the PIMD and the interface device;
   second communication circuitry provided in the housing and configured to effect communication between the interface device and a selected generic network access device of the plurality of generic network access devices;
   a processor coupled to memory, the first communication circuitry and the second communication circuitry, the processor and memory provided in the housing, and the processor configured to:
      translate medical information acquired from the PIMD via the interface device to account for the disparate communication protocols;
      control transmission of data including the translated medical information between the interface device and the selected generic network access device; and
      provide isolation between the PIMD and the selected generic network access device in compliance with a predetermined medical information regulatory standard governing the PIMD.

2. The device of claim 1, wherein the processor is further configured to push a protocol stack to the selected generic network access device, the protocol stack executable by the selected generic network access device to enable the processor to control one or more functions of the selected generic network access device.

3. The device of claim 1, wherein the processor is further configured to push a protocol stack to the selected generic network access device, the protocol stack executable by the selected generic network access device to enable the processor to control one or more communication functions of the selected generic network access device.

4. The device of claim 1, wherein the processor is further configured to push a protocol stack to the selected generic network access device, the protocol stack executable by the selected generic network access device to enable the processor to control communications with one or more external sensors via the selected generic network access device.

5. The device of claim 1, wherein the processor is further configured to push a protocol stack to the selected generic network access device, the protocol stack executable by the selected generic network access device to enable the processor to control presentation of information on a display or other output device of the selected generic network access device.

6. The device of claim 1, wherein the generic network access device is configured to connect with the public network infrastructure and facilitate transfer of information across a public communication network not specially certified to transfer medical information in a manner compliant with regulatory standards for handling medical information.

7. The device of claim 1, wherein the generic network access device comprises a mobile communications device.

8. The device of claim 1, wherein the generic network access device comprises a wired or wireless network access point.

9. The device of claim 1, wherein the generic network access device is configured to communicatively couple to the interface device via a hardwired connection.

10. The device of claim 9, wherein the hardwired connection comprises one or both of a communications connection and a power supply connection.

11. An interface device for facilitating transfer of medical information between a patient implantable medical device (PIMD) and a remote network server via public network infrastructure using any of a plurality of generic network access devices having disparate communication protocols, the interface device comprising:
   a housing configured for portability by an ambulatory patient;
   first communication circuitry provided in the housing and configured to effect communication between the PIMD and the interface device;
   second communication circuitry provided in the housing and configured to effect communication between the interface device and a selected generic network access device of the plurality of generic network access devices;
   a processor coupled to memory, the first communication circuitry and the second communication circuitry, the processor and memory provided in the housing, and the processor comprising:
      a unit configured to translate medical information acquired from the PIMD via the interface device to account for the disparate communication protocols;
      a unit configured to control transmission of data including the translated medical information between the interface device and the selected generic network access device; and
      means for isolating the PIMD and the selected generic network access device in compliance with a predetermined medical information regulatory standard governing the PIMD.

12. The device of claim 11, wherein the processor comprises means for pushing a protocol stack to the selected generic network access device, the protocol stack executable by the selected generic network access device to enable the processor to control one or more functions of the selected generic network access device.

13. The device of claim 11, wherein the processor comprises means for pushing a protocol stack to the selected generic network access device, the protocol stack executable by the selected generic network access device to enable the processor to control one or more communication functions of the selected generic network access device.

14. The device of claim 11, wherein the processor comprises means for pushing a protocol stack to the selected generic network access device, the protocol stack executable by the selected generic network access device to enable the processor to control communications with one or more external sensors via the selected generic network access device.

15. The device of claim 11, wherein the processor comprises means for pushing a protocol stack to the selected generic network access device, the protocol stack executable by the selected generic network access device to enable the processor to control presentation of information on a display or other output device of the selected generic network access device.

16. The device of claim 11, wherein the generic network access device is configured to connect with the public network infrastructure and facilitate transfer of information across a public communication network not specially certified to transfer medical information in a manner compliant with regulatory standards for handling medical information.

17. The device of claim 11, wherein the generic network access device comprises a mobile communications device.

18. The device of claim 11, wherein the generic network access device comprises a wired or wireless network access point.

19. The device of claim 11, wherein the generic network access device is configured to communicatively couple to the interface device via a hardwired connection.

20. The device of claim 19, wherein the hardwired connection comprises one or both of a communications connection and a power supply connection.

* * * * *